US012708641B2

(12) United States Patent
Jonckers et al.

(10) Patent No.: US 12,708,641 B2
(45) Date of Patent: Aug. 18, 2026

(54) BI- AND MONOCYCLIC NUCLEOSIDE ANALOGS FOR TREATMENT OF HEPATITIS E

(71) Applicant: JANSSEN PHARMACEUTICALS, INC., Titusville, NJ (US)

(72) Inventors: Tim Hugo Maria Jonckers, Heist-op-den-Berg (BE); Frederik Pauwels, Waasmunster (BE); Yannick Debing, Bilzen (BE)

(73) Assignee: Janssen Pharmaceuticals, Inc., Titusville, NJ (US)

(*) Notice: Subject to any disclaimer, the term of this patent is extended or adjusted under 35 U.S.C. 154(b) by 732 days.

(21) Appl. No.: 17/996,083

(22) PCT Filed: Apr. 13, 2021

(86) PCT No.: PCT/EP2021/059504

§ 371 (c)(1),
(2) Date: Oct. 13, 2022

(87) PCT Pub. No.: WO2021/209419

PCT Pub. Date: Oct. 21, 2021

(65) Prior Publication Data

US 2023/0310481 A1 Oct. 5, 2023

(30) Foreign Application Priority Data

Apr. 14, 2020 (EP) .................................... 20169480

(51) Int. Cl.
*A61K 31/7076* (2006.01)
*A61P 31/14* (2006.01)

(52) U.S. Cl.
CPC .......... *A61K 31/7076* (2013.01); *A61P 31/14* (2018.01)

(58) Field of Classification Search
None
See application file for complete search history.

(56) References Cited

U.S. PATENT DOCUMENTS

| | | | |
|---|---|---|---|
| 8,481,510 B2 | 7/2013 | Jonckers et al. | |
| 8,491,510 B2 | 7/2013 | Byrd et al. | |
| 8,933,052 B2 | 1/2015 | Jonckers et al. | |
| 9,006,209 B2 | 4/2015 | Jonckers et al. | |
| 9,012,428 B2 | 4/2015 | Jonckers et al. | |
| 9,108,999 B2 | 8/2015 | Zhang et al. | |
| 9,603,864 B2 * | 3/2017 | Blatt | A61P 31/14 |
| 11,267,844 B2 | 3/2022 | Tahri et al. | |
| 2015/0366888 A1 | 12/2015 | Blatt et al. | |
| 2017/0348343 A1 | 12/2017 | Bischofberger et al. | |

FOREIGN PATENT DOCUMENTS

| | | |
|---|---|---|
| JP | 2017-519784 A | 7/2017 |
| KR | 10-2014-0108290 A | 9/2014 |
| WO | 2010/130726 A1 | 11/2010 |
| WO | 2012/062869 A1 | 5/2012 |
| WO | 2012/062870 A1 | 5/2012 |
| WO | 2015/200219 A1 | 12/2015 |
| WO | 2016/069975 A1 | 5/2016 |
| WO | 2016/178876 A2 | 11/2016 |
| WO | 2017/189978 A1 | 11/2017 |
| WO | 2019/043177 A1 | 3/2019 |

OTHER PUBLICATIONS

Kamar, Nassim, et al. "Hepatitis E virus infection." Nature Reviews Disease Primers 3.1 (2017): 1-16.*

Bagshawe, "Antibody-Directed Enzyme Prodrug Therapy: A Review", Drug Development Research, 1995, 34, 220-230.

Berge et al., "Pharmaceutical Salts", Journal of Pharmaceutical Sciences, 1977, 66, 1-19.

Bertolini et al., "A New Rational Hypothesis for the Pharmacophore of the Active Metabolite of Leflunomide, a Potent Immunosuppressive Drug", J. Med. Chem, 1997, 40, 2011-2016.

Bodor., "Novel Approaches to the Design of Safer Drugs: Soft Drugs and Site-Specific Chemical Delivery Systems", Advance Drug Research, 1984, 13, 255-331, 77 pages.

Bundgaard, "Design of Prodrugs", Elsevier, 1985.

Considine, ed., Van Nostrand's Encyclopedia of Chemistry, 5th Ed., 2005, p. 261.

Comberg et al., "Sofosbuvir monotherapy fails to achieve HEV RNA elimination in patients with chronic hepatitis E—The HepNet SofE pilot study", J Hepatol, Sep. 2020, vol. 73, No. 3, pp. 696-699.

Debing et al., "A rat model for hepatitis E virus", Disease Models Mechanisms, 2016, 9, 1203-1210.

Debing et al., "Ribavirin in Vitro Hepatitis E virus replication through depletion of cellular GTP Pools and is Moderately synergistic with alpha interferon", Antimicrob agents chemother., 2013, 58, 267-273.

Donnelly et al., "Review article: hepatitis E—a concise review of virology, epidemiology, clinical presentation and therapy", Aliment Pharmacol Ther Jul. 2017, vol. 46, Issue 2, pp. 126-141.

Handbook of Pharmaceutical Salts, Properties, Selection, and Use, Stahl and Wermuth, Eds., Wiley-VCH and VHCA, Zurich, 2002.

Jain et al., "Synthesis and study of cyclic pronucleotides of 5-fluoro-2'-deoxyuridine", Bioorganic & Medical Chemistry Letters, 2012, vol. 22, 2012, 4497-4501.

Khimii, Journal of General Chemistry of the USSR, 1965, vol. 35, p. 1462-1464.

Krogsgaard-Larsen et al., "Design and Application of Products, Drug Design and Development", Hardwood Academic Publishers, 1991.

Li et al., "Efficient Synthesis of Methyl 3,5-Di-O-benzyl-r-D-ribofuranoside and Application to the Synthesis of 2'-C—Alkoxymethyluridines", Org. Lett., 2007, 9, 3009-3012.

Netzler et al., "Abstract", Antimicrobial Agents and Chemotherapy, vol. 63, No. 6, Mar. 18, 2019.

(Continued)

*Primary Examiner* — Patrick T Lewis
(74) *Attorney, Agent, or Firm* — BakerHostetler

(57) ABSTRACT

The present disclosure is directed toward bi- and monocyclic nucleoside analogs, and compositions comprising these compounds for use in the treatment of hepatitis E infections.

7 Claims, No Drawings

(56) References Cited

OTHER PUBLICATIONS

Paulekuhn et al., "Trends in Active Pharmaceutical Pharmaceutical Ingredient Salt Selection based on Analysis of the Orange Book Database", J. Med. Chem., 2007, 50, 6665-6672.
Remington's Pharmaceutical Sciences, Genaro, Ed., Mack Publishing Co., 1985, Easton PA.
Shan et al., "Prodruq Strategies Based on Intramolecular Cyclization Reactions", Journal of Pharmaceutical Sciences, 1997, 86(7), 765-767.
Shukla et al., "Adaptation of a genotype 3 hepatitis E virus to efficient growth in cell culture depends on an inserted human gene segment acquired by recombination", Journal of Virology., 2012, 86, 5697-5707.
Netzler et al., "Antiviral Candidates for Treating Hepatitis E Virus Infection", Antimicrobial Agents and Chemotherapy, Jun. 2019, 63(6), pp. 1-24.
Thi et al., "Sofosbuvir Inhibits Hepatitis E Virus Replication In Vitro and Results in an Additive Effect When Combined With Ribavirin", Gastroenterology 2015, 150(1), pp. 82-85 and e1-e4.

* cited by examiner

BI- AND MONOCYCLIC NUCLEOSIDE ANALOGS FOR TREATMENT OF HEPATITIS E

CROSS-REFERENCE TO RELATED APPLICATIONS

This application is the US National Stage Application of International Patent Application No. PCT/EP2021/059504, filed Apr. 13, 2021, which claims the benefit of the priority of European Patent Application No. 20169480.9, filed Apr. 14, 2020, the disclosures of which are incorporated herein by reference in their entireties.

BACKGROUND

Hepatitis E virus (HEV) is believed to be the cause of about 20 million human infections a year and the most common cause of acute hepatitis and jaundice worldwide. Immuno-compromised patients are a significant population at risk for chronic HEV infection. Acute HEV infections tend to be self-limiting, but HEV genotype 3 can persist in immune-compromised patients, especially organ transplant recipients, leading to chronic hepatitis, cirrhosis and/or liver failure.

HEV is a positive-sense, single-stranded, nonenveloped, RNA icosahedral virus classified in the genus Orthohepevirus and the family Hepeviridae. Although HEV genotype 1 and 2 infect only humans, genotypes 3 and 4 also infect swine and other types of animals. Each of the four genotypes is classified into multiple subtypes.

HEV infections have been treated by ribavirin (RBV) and pegylated interferon-α with varying success. Accordingly, there is still a need for safe, tolerable and effective treatment options for HEV infections.

SUMMARY

Provided herein are compounds, more particularly methods of ameliorating and/or treating a Hepatitis E (HEV) infection, as well as compounds for use in such treatment.

In an aspect, provided herein are compounds, more particularly compounds for use in treating a hepatitis E infection in a subject in need thereof, wherein the compound is a compound of formula (I):

(I)

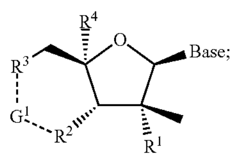

or a pharmaceutically acceptable salt thereof;

wherein:

Base is selected from the group consisting of (b-1), (b-2), (b-3), (b-4), (b-5), (b-6), (b-7), and (b-8):

(b-1)

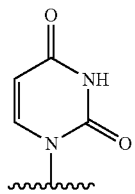

-continued (b-2)

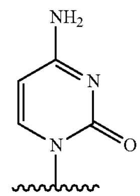

(b-3)

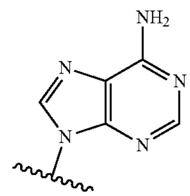

(b-4)

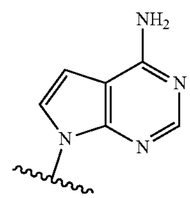

(b-5)

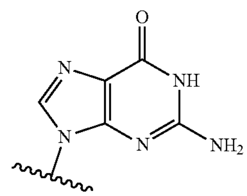

(b-6)

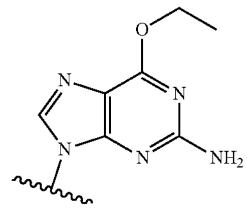

(b-7)

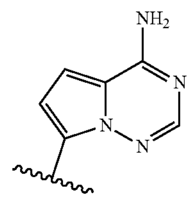

(b-8)

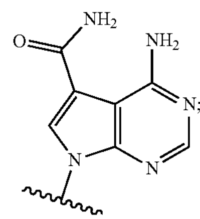

$R^1$ is selected from the group consisting of OH and F;

$G^1$ is absent, or $G^1$ is selected from the group consisting of (g-1), (g-2), and (g-3):

(g-1)

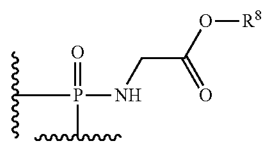

(g-2)

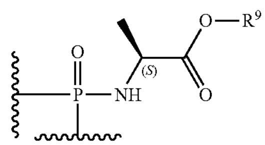

(g-3)

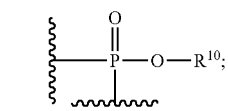

'--' is a bond when $G^1$ is selected from the group consisting of (g-1), (g-2), and (g-3); and '--' is absent when $G^1$ is absent;

$R^8$ is selected from the group consisting of $C_{1-4}$alkyl and $C_{3-6}$cycloalkyl;

$R^9$ is $C_{1-4}$alkyl;

$R^{10}$ is selected from the group consisting of $C_{2-3}$alkenyl and $C_{3-6}$cycloalkyl; wherein when $G^1$ is absent;

$R^2$ is OH when $G^1$ is absent; and $R^2$ is —O— when $G^1$ is selected from the group consisting of (g-1), (g-2), and (g-3);

$R^3$ is —O— when $G^1$ is selected from the group consisting of (g-1), (g-2), and (g-3); and $R^3$ is selected from the group consisting of (f-1), (f-2), and (f-3) when $G^1$ is absent:

(f-1)

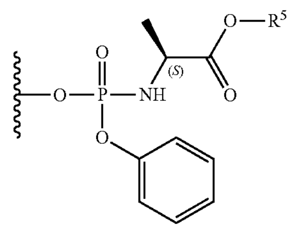

(f-2)

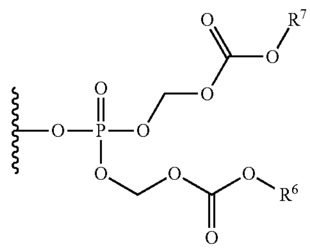

(f-3)

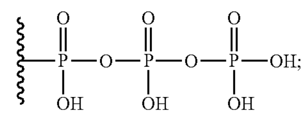

$R^5$ is selected from the group consisting of $C_{1-4}$alkyl and $C_{3-6}$cycloalkyl;

$R^6$ is selected from the group consisting of $C_{1-4}$alkyl and $C_{3-6}$cycloalkyl; and $R^7$ is C-4alkyl;

wherein when $G^1$ is present;

$R^2$ is O;

$R^3$ is O; and $R^4$ is selected from the group consisting of H and F.

In an embodiment, Base is selected from the group consisting of (b-1) and (b-6). In another embodiment wherein $G^1$ is absent, $R^3$ is selected from the group consisting of (f-1) and (f-2). In yet another embodiment, $G^1$ is (g-1) and $R^8$ is $C_{1-4}$alkyl. In still another embodiment, $G^1$ is (g-2). In another embodiment, $G^1$ is (g-3) and $R^{10}$ is selected from $C_{1-4}$alkyl and $C_{2-3}$alkenyl.

In an embodiment, the compound is selected from the group consisting of:

1

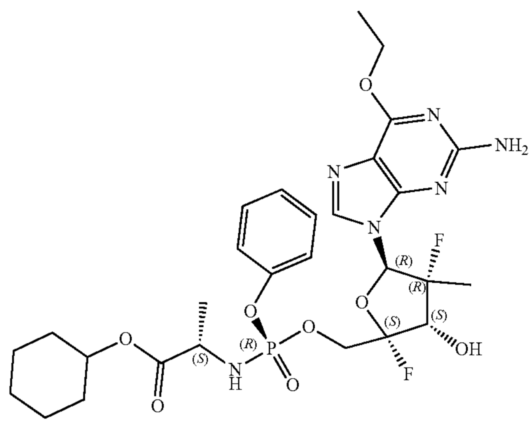

2

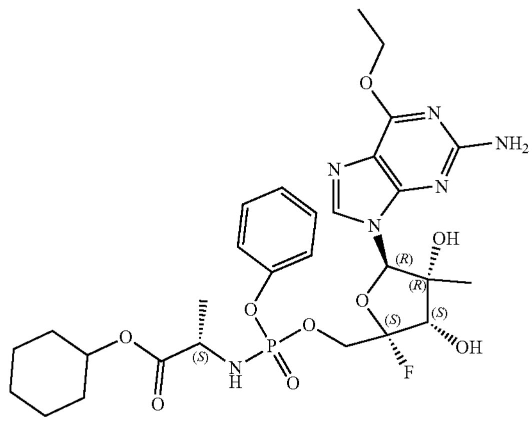

3

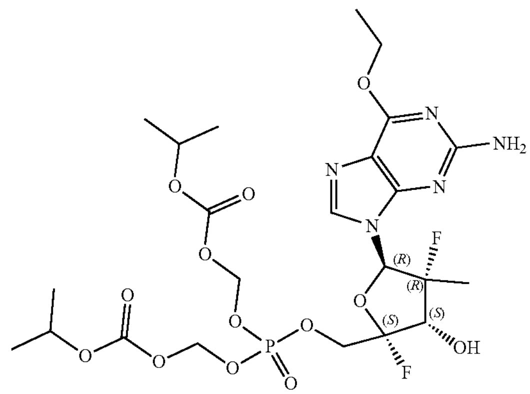

-continued

4

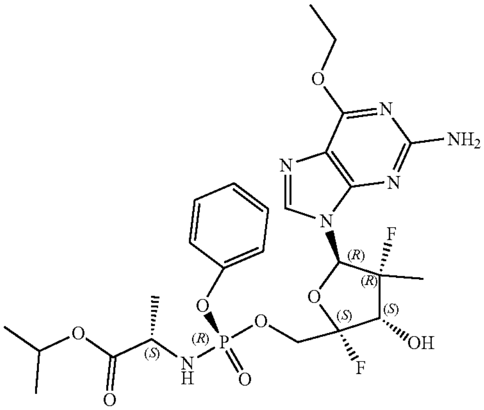

5

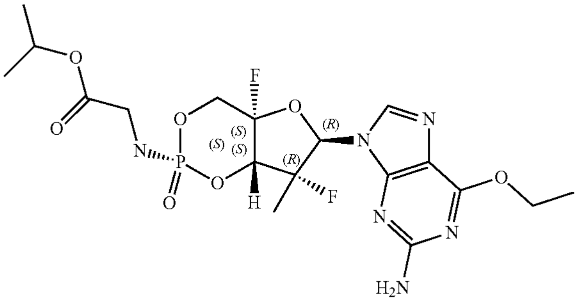

6

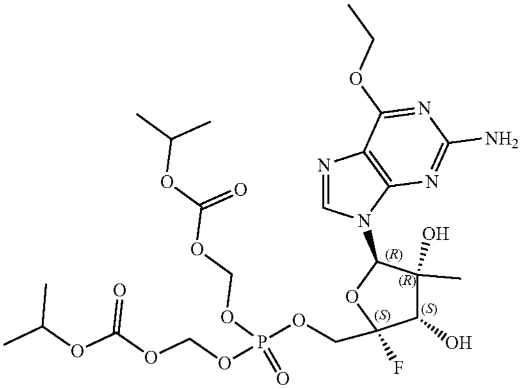

7

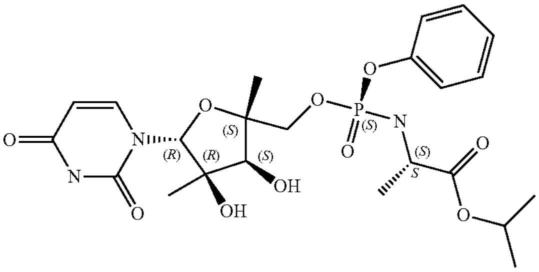

8

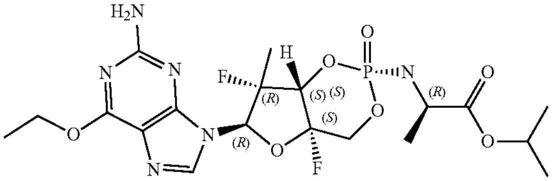

-continued

9

10

11

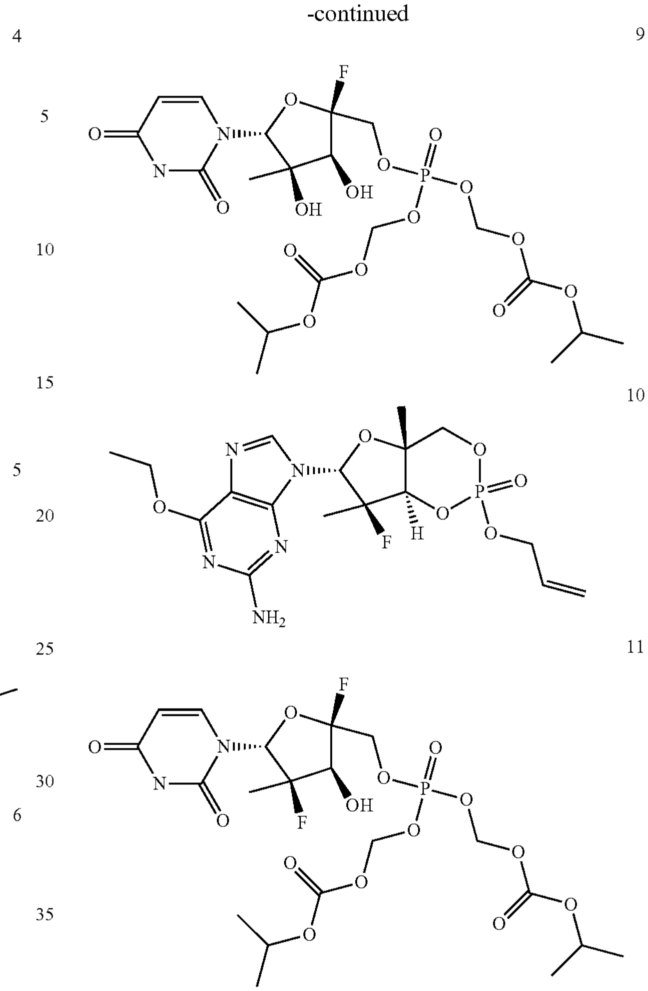

or pharmaceutically acceptable salts thereof.

In another aspect, provided herein are pharmaceutical compositions for use in treating a hepatitis E infection in a subject in need thereof, which comprises the compounds disclosed herein, and a pharmaceutically acceptable vehicle.

In an embodiment, the hepatitis E infection is a chronic HEV infection. In another embodiment, the HEV infection is of genotype 1, genotype 2 or genotype 3. In yet another embodiment, the subject is a pregnant woman, an immune-compromised subject or immune-deficient subject.

DETAILED DESCRIPTION

Provided herein are compounds, more particularly methods of ameliorating and/or treating a Hepatitis E (HEV) infection, as well as compounds for use in such treatment. In an aspect, provided herein are compounds of Formula (I) which can be used for treatment of Hepatitis E viral infections. Also provided herein are pharmaceutical compositions comprising compounds of Formula (I).

Definitions

Listed below are definitions of various terms used to describe this present disclosure. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the applicable art. Generally, the nomenclature used herein and the laboratory procedures in cell culture, molecular genetics, organic chemistry, and peptide chemistry are those well-known and commonly employed in the art.

As used herein, the articles “a” and “an” refer to one or to more than one (i.e. to at least one) of the grammatical object of the article. By way of example, “an element” means one element or more than one element. Furthermore, use of the term “including” as well as other forms, such as “include,” “includes,” and “included,” is not limiting.

As used in the specification and in the claims, the term “comprising” can include the embodiments “consisting of” and “consisting essentially of” The terms “comprise(s),” “include(s),” “having,” “has,” “can,” “contain(s),” and variants thereof, as used herein, are intended to be open-ended transitional phrases, terms, or words that require the presence of the named ingredients/steps and permit the presence of other ingredients/steps. However, such description should be construed as also describing compositions or processes as “consisting of” and “consisting essentially of” the enumerated compounds, which allows the presence of only the named compounds, along with any pharmaceutically acceptable carriers, and excludes other compounds.

All ranges disclosed herein are inclusive of the recited endpoint and independently combinable (for example, the range of “from 50 mg to 300 mg” is inclusive of the endpoints, 50 mg and 300 mg, and all the intermediate values). The endpoints of the ranges and any values disclosed herein are not limited to the precise range or value; they are sufficiently imprecise to include values approximating these ranges and/or values.

As used herein, approximating language can be applied to modify any quantitative representation that can vary without resulting in a change in the basic function to which it is related. In at least some instances, the approximating language can correspond to the precision of an instrument for measuring the value.

The term “alkyl” refers to a straight- or branched-chain alkyl group having from 1 to 12 carbon atoms in the chain. Examples of alkyl groups include methyl (Me, which also may be structurally depicted by the symbol, “/”), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-4}$alkyl as used here refers to a straight- or branched-chain alkyl group having from 1 to 4 carbon atoms in the chain. The term $C_{1-6}$alkyl as used here refers to a straight- or branched-chain alkyl group having from 1 to 6 carbon atoms in the chain.

The term “cycloalkyl” refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

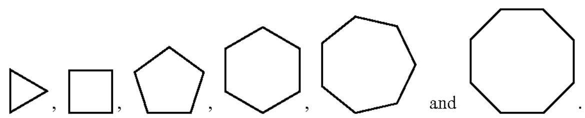

, , , , and .

A monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hickel).

Particular examples of monocyclic, bicyclic or tricyclic aromatic carbocycles are phenyl, naphthalenyl, anthracenyl.

The term “phenyl” represents the following moiety:

.

The term “heteroaryl” refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, oxazolyl, thiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

Those skilled in the art will recognize that the species of heteroaryl groups listed or illustrated above are not exhaustive, and that additional species within the scope of these defined terms may also be selected.

The term “substituted” means that the specified group or moiety bears one or more substituents. The term “unsubstituted” means that the specified group bears no substituents. The term “optionally substituted” means that the specified group is unsubstituted or substituted by one or more substituents. Where the term “substituted” is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

To provide a more concise description, some of the quantitative expressions given herein are not qualified with the term “about.” It is understood that, whether the term “about” is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions.

Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of n electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base. For example, all tautomers of a phosphate and a phosphorothioate groups are intended to be included. Examples of tautomers of a phosphorothioate include the following:

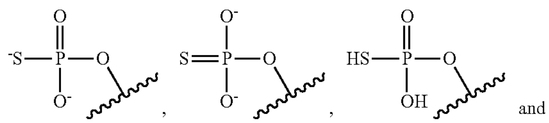

and

-continued

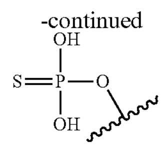

Furthermore, all tautomers of heterocyclic bases known in the art are intended to be included, including tautomers of natural and non-natural purine-bases and pyrimidine-bases.

Tautomeric forms may be relevant to the attainment of the optimal chemical reactivity and biological activity of a compound of interest.

The compounds of this present disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) or (*R) or (*S) is used in the name to indicate that the absolute stereochemistry of the corresponding stereocenter is unknown. Thus, a compound designated as (R*) or (*R) refers to an enantiopure compound with an absolute configuration of either (R) or (S). In cases where the absolute stereochemistry has been confirmed, the structures are named using (R) and (S).

The symbols 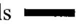 and 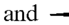 are used as meaning the same spatial arrangement in chemical structures shown herein. Analogously, the symbols  and 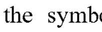 are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I), or pharmaceutically acceptable salts of compounds of Formula (I), may be obtained as solvates. Solvates include those formed from the interaction or complexation of compounds of the present disclosure with one or more solvents, either in solution or as a solid or crystalline form. In some embodiments, the solvent is water and the solvates are hydrates. In addition, certain crystalline forms of compounds of Formula (I), or pharmaceutically acceptable salts of compounds of Formula (I) may be obtained as co-crystals. In certain embodiments of the present disclosure, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named.

For example, reference herein to a compound such as R—COOH, encompasses reference to any one of, for example, $R—COOH_{(s)}$, $R—COOH_{(sol)}$, and $R—COO^-_{(sol)}$. In this example, $R—COOH_{(s)}$ refers to the solid compound, as it could be for example in a tablet or some other solid pharmaceutical composition or preparation; $R—COOH_{(sol)}$ refers to the undissociated form of the compound in a solvent; and $R—COO^-_{(sol)}$ refers to the dissociated form of the compound in a solvent, such as the dissociated form of the compound in an aqueous environment, whether such dissociated form derives from R—COOH, from a salt thereof, or from any other entity that yields $R—COO^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as $R—COOH_{(aq)}$ and/or $R—COO^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts." Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this present disclosure, as would in any case be so appreciated by those of ordinary skill in the art. Because there is no need to name each and every embodiment that would be recognized by those of ordinary skill in the art, no structures of the zwitterionic compounds that are associated with the compounds of this present disclosure are given explicitly herein. They are, however, part of the embodiments of this present disclosure. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorus, sulfur, fluorine, chlorine, and iodine such as $^2H$, $^3H$, $^{11}C$, $^{13}C$, $^{14}C$ $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example deuterium (i.e., D or $^2H$); or tritium (i.e., T or $^3H$)), detection or imaging techniques such as positron emission tomography (PET) or single-photon emission computed tomography (SPECT) including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this present disclosure and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this present disclosure given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $G^1$, $G^2$, $G^3$, $G^4$, $G^5$, $G^6$, $G^7$, $G^8$, $G^9$, $G^{10}$, $G^{11}$, n, L, R, T, Q, W, X, Y, and Z and any other generic substituent symbol used herein.

Furthermore, when more than one assignment is given for any member or substituent, embodiments of this present disclosure comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this present disclosure for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of Si, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $G^1$, $G^2$, $G^3$, $G^4$, $G^5$, $G^6$, $G^7$, $G^1$, $G^9$, $G^{10}$, $G^{11}$, n, L, R, T, Q, W, X, Y, and Z and any other generic substituent symbol used herein.

The nomenclature "$C_{i-j}$" with j>i, when applied herein to a class of substituents, is meant to refer to embodiments of this present disclosure for which each and every one of the number of carbon members, from i to j including i and j, is independently realized. By way of example, the term $C_{1-4}$ refers independently to embodiments that have one carbon member ($C_1$), embodiments that have two carbon members ($C_2$), embodiments that have three carbon members ($C_3$), and embodiments that have four carbon members ($C_4$).

The term $C_{n-m}$alkyl refers to an aliphatic chain, whether straight or branched, with a total number N of carbon members in the chain that satisfies $n \leq N \leq m$, with m>n. Any disubstituent referred to herein is meant to encompass the various attachment possibilities when more than one of such possibilities are allowed. For example, reference to disubstituent -A-B—, where $A \neq B$, refers herein to such disubstituent with A attached to a first substituted member and B attached to a second substituted member, and it also refers to such disubstituent with A attached to the second substituted member and B attached to the first substituted member.

The present disclosure includes also pharmaceutically acceptable salts of the compounds of Formula (I), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

A "pharmaceutically acceptable salt" is intended to mean a salt of a free acid or base of compounds represented by Formula (I) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

The present disclosure also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

The present disclosure also relates to pharmaceutically active metabolites of the compounds of Formula (I), which may also be used in the methods of the present disclosure. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

As used herein, the term "composition" or "pharmaceutical composition" refers to a mixture of at least one compound provided herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound provided herein within or to the patient such that it can perform its intended function. Typically, such constructs are carried or transported from one organ, or portion of the body, to another organ, or portion of the body. Each carrier must be "acceptable" in the sense of being compatible with the other ingredients of the formulation, including the compound provided herein, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound provided herein, and are physiologically acceptable to the patient. Supplementary active compounds can also be incorporated into the compositions. The "pharmaceutically acceptable carrier" can further include a pharmaceutically acceptable salt of the compound provided herein. Other additional ingredients that can be included in the pharmaceutical compositions provided herein are known in the art and described, for example in Remington's Pharmaceutical Sciences (Genaro, Ed., Mack Publishing Co., 1985, Easton, PA), which is incorporated herein by reference.

As used herein, the term "physiologically acceptable" refers to a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The term "stabilizer," as used herein, refers to polymers capable of chemically inhibiting or preventing degradation of a compound of Formula I. Stabilizers are added to formulations of compounds to improve chemical and physical stability of the compound.

The term "tablet," as used herein, denotes an orally administrable, single-dose, solid dosage form that can be produced by compressing a drug substance or a pharmaceutically acceptable salt thereof, with suitable excipients (e.g., fillers, disintegrants, lubricants, glidants, and/or surfactants) by conventional tableting processes. The tablet can be produced using conventional granulation methods, for example, wet or dry granulation, with optional comminution of the granules with subsequent compression and optional coating. The tablet can also be produced by spray-drying.

As used herein, the term "capsule" refers to a solid dosage form in which the drug is enclosed within either a hard or soft soluble container or "shell." The container or shell can be formed from gelatin, starch and/or other suitable substances.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

The term "combination," "therapeutic combination," "pharmaceutical combination," or "combination product" as used herein refer to a non-fixed combination or a kit of parts for the combined administration where two or more therapeutic agents can be administered independently, at the same time or separately within time intervals, especially where these time intervals allow that the combination partners show a cooperative, e.g., synergistic, effect.

The term "modulators" include both inhibitors and activators, where "inhibitors" refer to compounds that decrease, prevent, inactivate, desensitize, or down-regulate HEV assembly and other HEV core protein functions necessary for HEV replication or the generation of infectious particles.

As used herein, the term "treatment" or "treating," is defined as the application or administration of a therapeutic agent, i.e., a compound of the present disclosure (alone or in combination with another pharmaceutical agent), to a patient, or application or administration of a therapeutic agent to an isolated tissue or cell line from a patient (e.g., for diagnosis or ex vivo applications), who has an HEV infection, a symptom of HEV infection or the potential to develop an HEV infection, with the purpose to cure, heal, alleviate, relieve, alter, remedy, ameliorate, improve or affect the HEV infection, the symptoms of HEV infection or the potential to develop an HEV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

In treatment methods according to the present disclosure, an effective amount of a pharmaceutical agent according to the present disclosure is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID, and, in an embodiment, BID). An example of a dose is in the range of from about 10 to about 300 mg of compound per kg of subject's body weight per day, in an embodiment about 15 to 250 mg/kg/day, or about 20 to 200 mg/kg/day, in single or divided dosage units (e.g., BID, TID, QID, and, in an embodiment, BID). A high dose may be about 200 mg/kg/day, while a medium dose may be about 70 mg/kg/day and a low dose may be about 20 mg/kg/day. For a 70-kg human, an illustrative range for a suitable dosage amount is from about 0.05 to about 7 g/day, or about 0.2 to about 2.5 g/day.

An example of a dose of a compound is from about 1 mg to about 2,500 mg. In some embodiments, a dose of a compound of the present disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HEV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

Compounds

In an aspect, provided herein are compounds of formula (I)

(I)

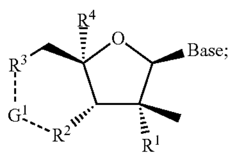

or a pharmaceutically acceptable salt thereof;

wherein:

Base is selected from the group consisting of (b-1), (b-2), (b-3), (b-4), (b-5), (b-6), (b-7), and (b-8):

(b-1)

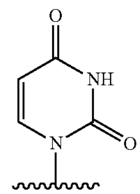

(b-2)

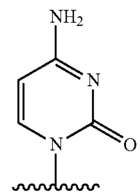

(b-3)

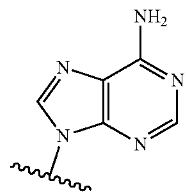

(b-4)

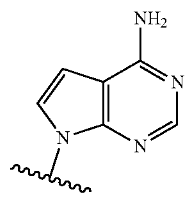

(b-5)

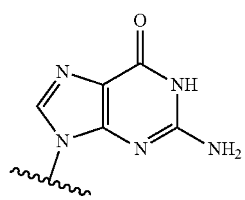

(b-6)

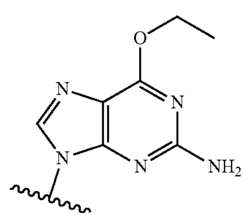

(b-7)

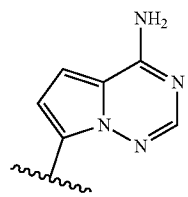

-continued (b-8)

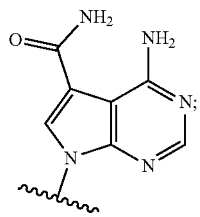

$R^1$ is selected from the group consisting of OH and F;

$G^1$ is absent, or $G^1$ is selected from the group consisting of (g-1), (g-2), and (g-3):

(g-1)

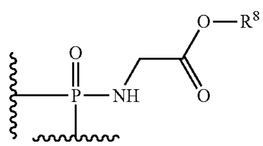

(g-2)

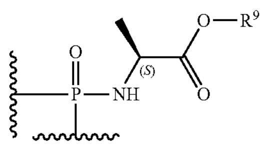

(g-3)

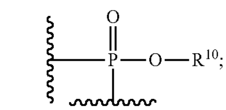

'--' is a bond when $G^1$ is selected from the group consisting of (g-1), (g-2), and (g-3); and '--' is absent when $G^1$ is absent;

$R^8$ is selected from the group consisting of $C_{1-4}$alkyl and $C_{3-6}$cycloalkyl;

$R^9$ is $C_{1-4}$alkyl;

$R^{10}$ is selected from the group consisting of $C_{2-3}$alkenyl and $C_{3-6}$cycloalkyl; wherein when $G^1$ is absent;

$R^2$ is OH when $G^1$ is absent; and $R^2$ is —O— when $G^1$ is selected from the group consisting of (g-1), (g-2), and (g-3);

$R^3$ is —O— when $G^1$ is selected from the group consisting of (g-1), (g-2), and (g-3); and $R^3$ is selected from the group consisting of (f-1), (f-2) and (f-3) when $G^1$ is absent:

(f-1)

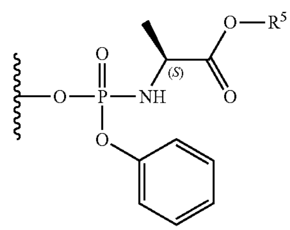

-continued (f-2)

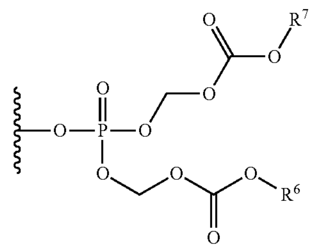

(f-3)

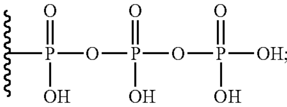

$R^5$ is selected from the group consisting of $C_{1-4}$alkyl and $C_{3-6}$cycloalkyl;

$R^6$ is selected from the group consisting of $C_{1-4}$alkyl and $C_{3-6}$cycloalkyl; and $R^7$ is $C_{1-4}$alkyl;

wherein when $G^1$ is present;

$R^2$ is O;

$R^3$ is O; and $R^4$ is selected from the group consisting of H and F.

In an embodiment, Base is selected from the group consisting of a group of formula (b-1) and a group of formula (b-6). In another embodiment, wherein $G^1$ is absent, $R^3$ is selected from the group consisting of (f-1) and (f-2). In yet another embodiment, $G^1$ is (g-1) and $R^8$ is $C_{1-4}$alkyl. In still another embodiment, $G^1$ is (g-2). In another embodiment, $G^1$ is (g-3) and $R^{10}$ is selected from $C_{1-4}$alkyl and $C_{2-3}$alkenyl. In another embodiment, $R^5$ is $C_6$-cycloalkyl.

In an embodiment, the compound of Formula (I) is selected from the group consisting of:

1

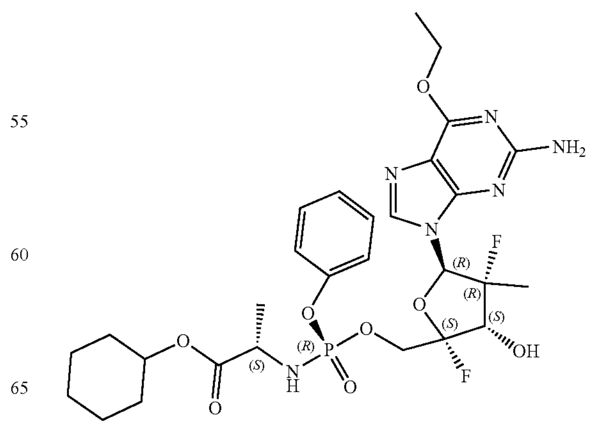

-continued
2
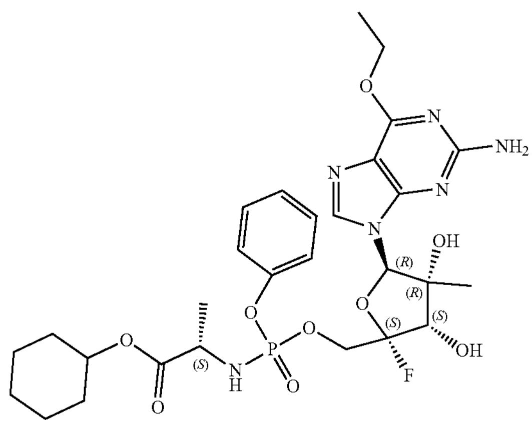
3
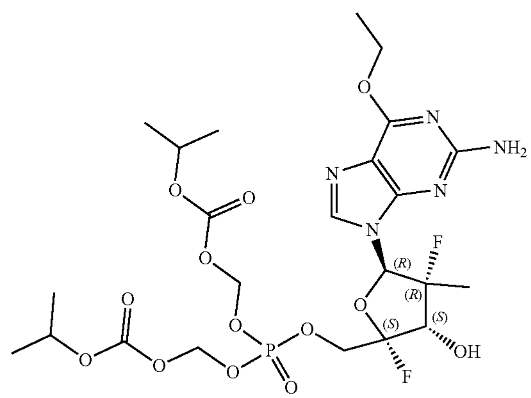
4
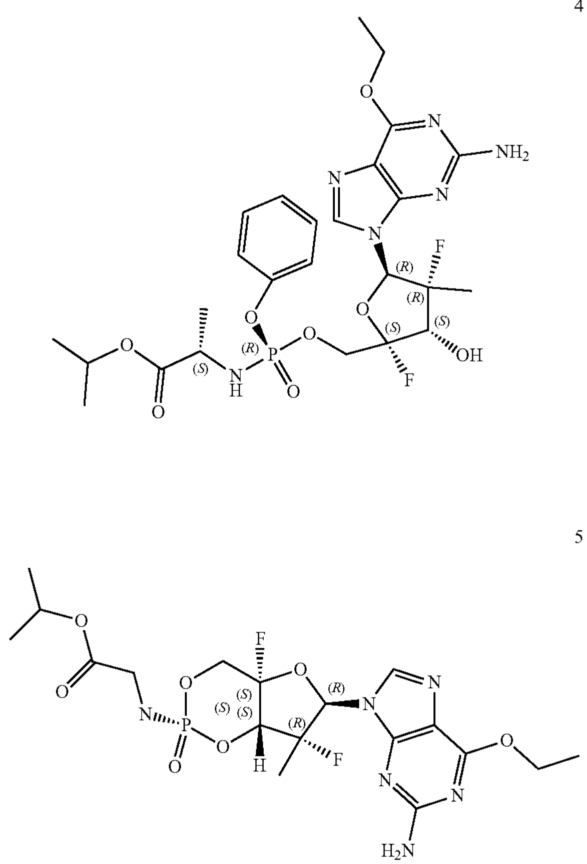
5
-continued
6
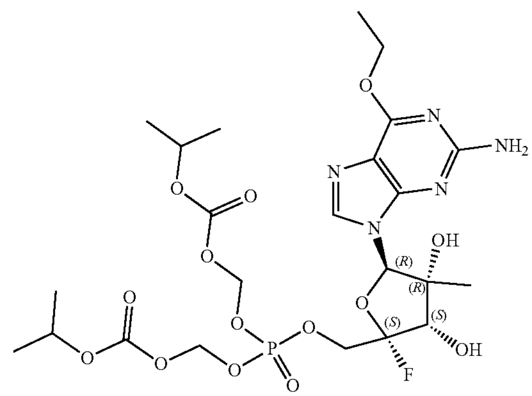
7
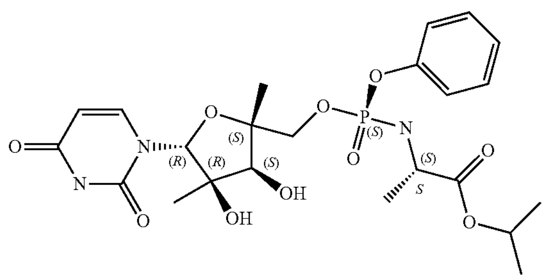
8
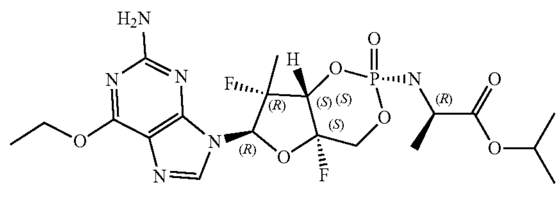
9
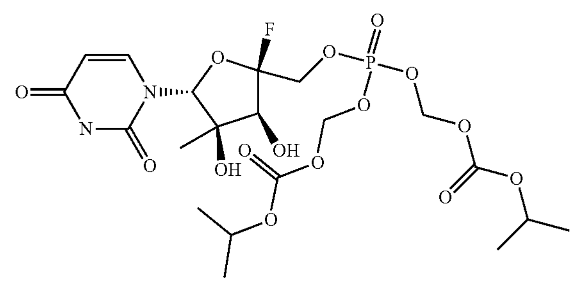
10
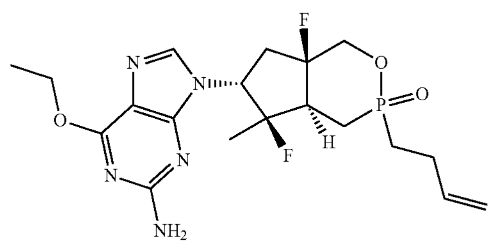

-continued

11

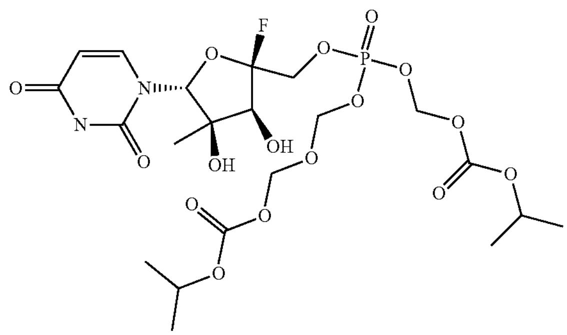

or pharmaceutically acceptable salts thereof.

In an embodiment, the compound is not isopropyl (2S)-2-[[[(2R,3R,4R,5R)-5-(2,4-dioxopyrimidin-1-yl)-4-fluoro-3-hydroxy-4-methyltetrahydrofuran-2-yl]methoxy-phenoxy-phosphoryl]amino]propanoate:

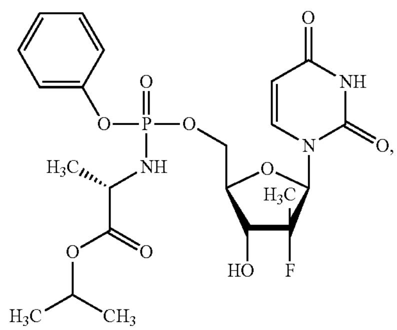

or a pharmaceutically acceptable salt thereof.

In an embodiment, the compound is:

4

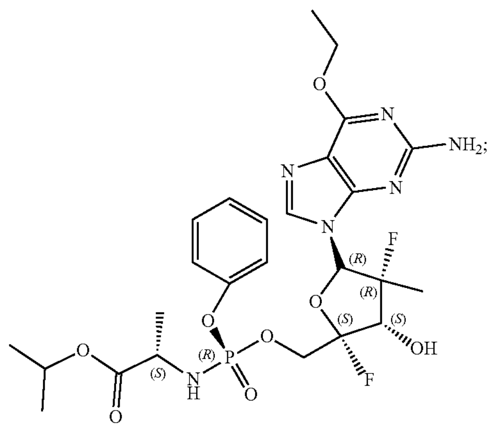

or a pharmaceutically acceptable salt thereof.

In another aspect, provided herein are compounds of formula (Ia)

(Ia)

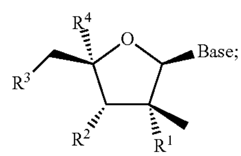

or a pharmaceutically acceptable salt thereof;

wherein:

Base is selected from the group consisting of (b-1) and (b-6):

(b-1)

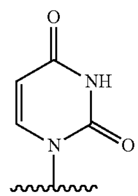

(b-6)

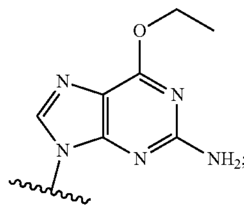

$R^1$ is selected from the group consisting of OH and F;

$R^2$ is OH;

$R^3$ is selected from the group consisting of (f-1) and (f-2):

(f-1)

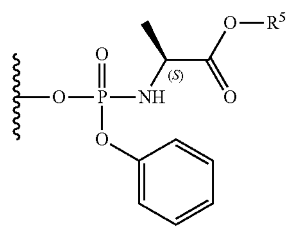

(f-2)

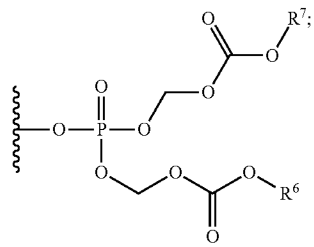

$R^4$ is F;

$R^5$ is selected from the group consisting of $C_{1-4}$alkyl and $C_{3-6}$cycloalkyl;

$R^6$ is selected from the group consisting of $C_{1-4}$alkyl and $C_{3-6}$cycloalkyl; and $R^7$ is $C_{1-4}$alkyl.

In an embodiment of formula (Ia), $R^5$ is $C_6$-cycloalkyl.

In an embodiment, the compound of Formula (Ia) is selected from the group consisting of:
1
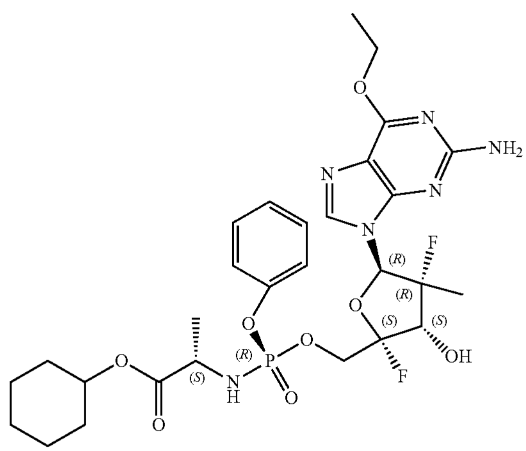
2
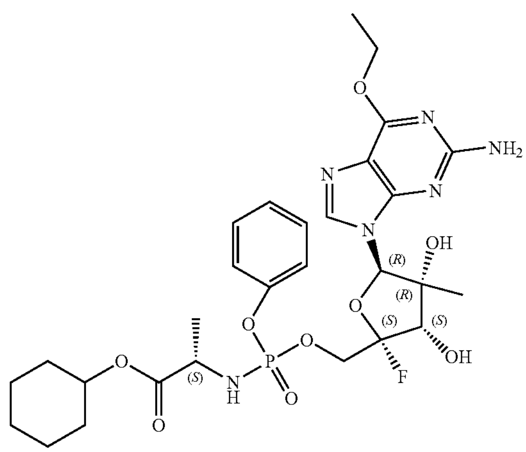
3
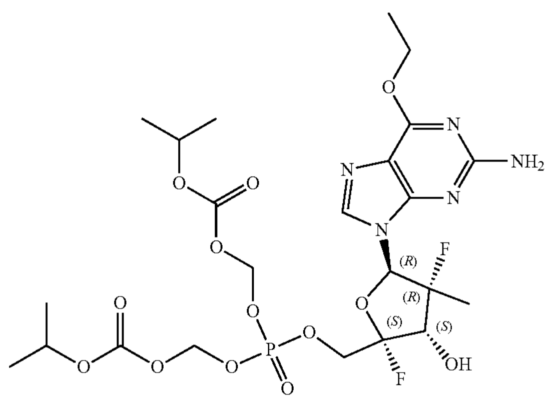
-continued
4
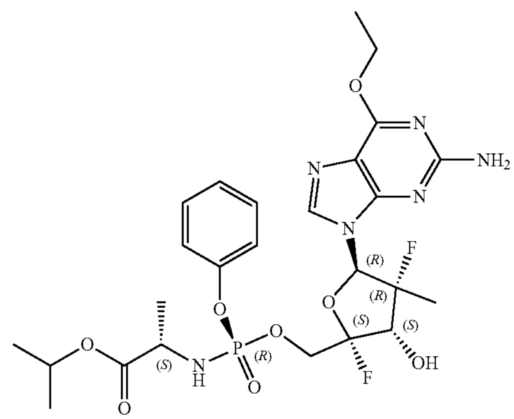
6
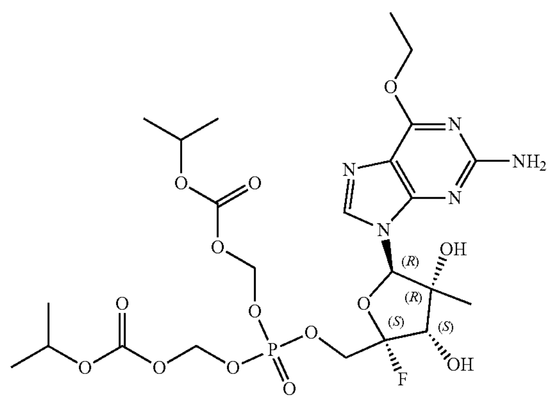
7
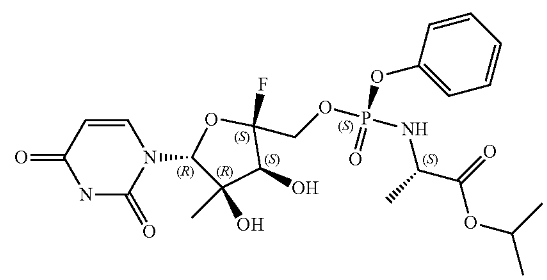
9
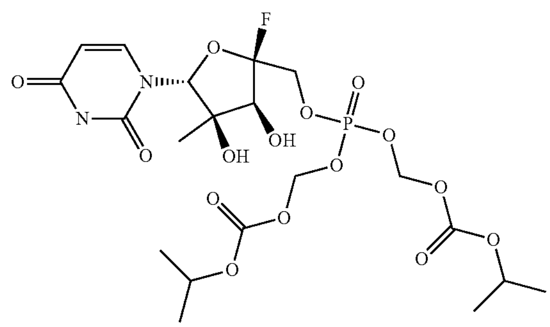

-continued

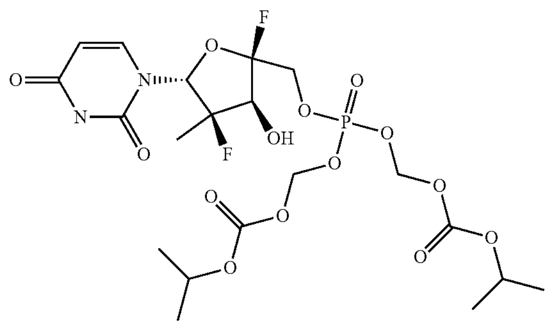

or a pharmaceutically acceptable salt thereof.

In an embodiment, the compound is not isopropyl (2S)-2-[[[(2R,3R,4R,5R)-5-(2,4-dioxopyrimidin-1-yl)-4-fluoro-3-hydroxy-4-methyltetrahydrofuran-2-yl]methoxy-phenoxy-phosphoryl]amino]propanoate:

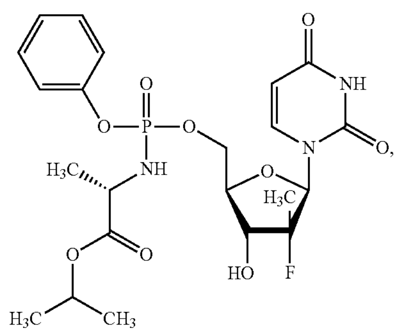

or a pharmaceutically acceptable salt thereof.

In an embodiment of Formula (Ia), the compound is:

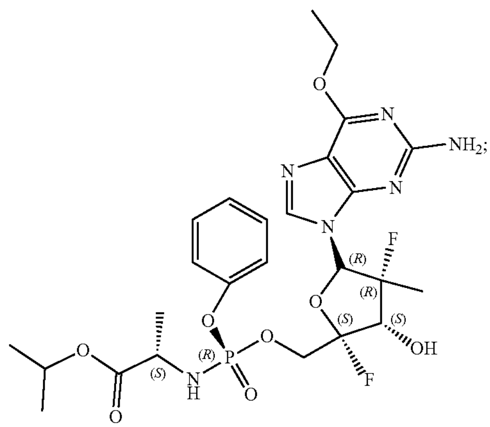

or a pharmaceutically acceptable salt thereof.

In yet another aspect, provided herein are compounds of Formula (Ib):

(Ib)

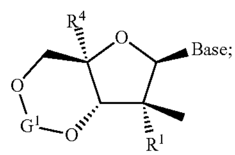

or a pharmaceutically acceptable salt thereof;

wherein:

Base is (b-6):

(b-6)

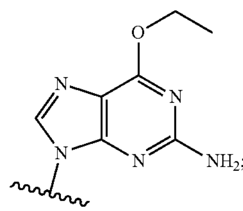

$R^1$ is F;

$R^4$ is selected from the group consisting of H and F;

$G^1$ is selected from the group consisting of (g-1), (g-2) and (g-3):

(g-1)

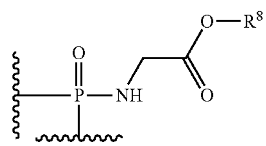

(g-2)

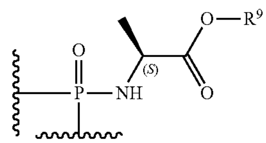

(g-3)

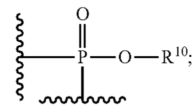

'--' is a bond $R^8$ is selected from the group consisting of $C_{1-4}$alkyl and $C_{3-6}$cycloalkyl;

$R^9$ is $C_{1-4}$alkyl; and $R^{10}$ is selected from the group consisting of $C_{2-3}$alkenyl and $C_{3-6}$cycloalkyl.

In an embodiment of Formula Ib, $G^1$ is (g-1) and $R^8$ is $C_{1-4}$alkyl. In yet another embodiment of Formula Ib, $G^1$ is (g-2). In still another embodiment of Formula Ib, $G^1$ is (g-3) and $R^{10}$ is selected from $C_{1-4}$alkyl and $C_{2-3}$alkenyl. In another embodiment of Formula Ib, $R^5$ is $C_6$-cycloalkyl.

In an embodiment, the compound of Formula (Ib) is selected from the group consisting of:

5

8

10

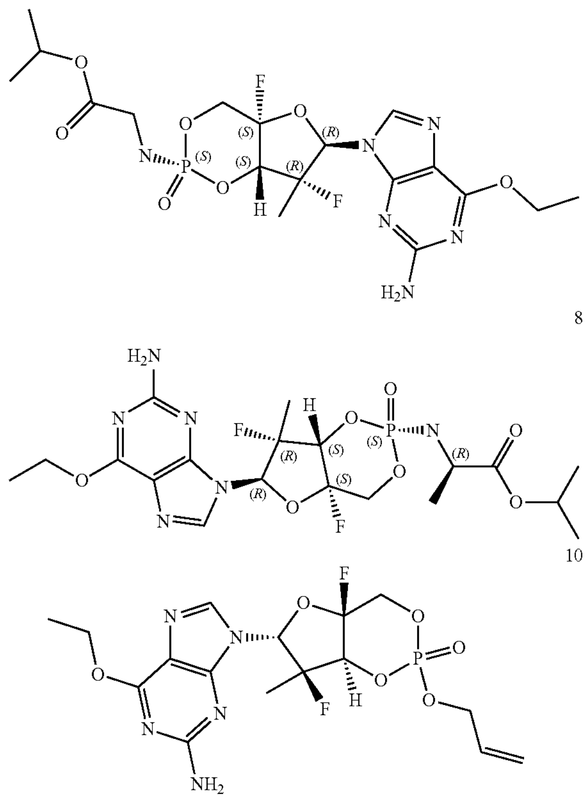

or a pharmaceutically acceptable salt thereof.

Compounds of the Formulae (I), (Ia), and (Ib) may be prepared by methods known to those skilled in the art and/or by variants of such methods using routine experimentation guided by the teachings provided herein.

Pharmaceutical Compositions

Also provided herein are pharmaceutical compositions comprising at least one compound of Formula I and at least one pharmaceutically acceptable excipient.

Some embodiments described herein relate to the use of a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen.

Techniques for formulation and administration of the compounds described herein are known to those skilled in the art.

As used herein, the term "composition" or "pharmaceutical composition" refers to a mixture of at least one compound useful within the present disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the present disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the present disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure and are physiologically acceptable to the patient. Supplementary active compounds may also be incorporated into the compositions. The "pharmaceutically acceptable carrier" may further include a pharmaceutically acceptable salt of the compound useful within the present disclosure. Other additional ingredients that may be included in the pharmaceutical compositions used in the practice of the present disclosure are known in the art and described, for example in Remington's Pharmaceutical Sciences (Genaro, Ed., Mack Publishing Co., 1985, Easton, PA), which is incorporated herein by reference.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the present disclosure can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the present disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract or may be coated with an enteric coating.

Capsules for oral administration include hard and soft gelatin capsules. To prepare hard gelatin capsules, compounds of the present disclosure may be mixed with a solid, semi-solid, or liquid diluent. Soft gelatin capsules may be prepared by mixing the compound of the present disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this present disclosure may also be administered by non-oral routes. For example, the compositions may be formulated for rectal administration as a suppository. For parenteral use, including intravenous, intramuscular, intraperitoneal, or subcutaneous routes, the compounds of the present disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle.

Another mode of administering the compounds of the present disclosure may utilize a patch formulation to affect transdermal delivery.

Compounds of the present disclosure may alternatively be administered in methods of this present disclosure by inhalation, via the nasal or oral routes, e.g., in a spray formulation also containing a suitable carrier.

Methods of Treatment

Provided herein are methods of ameliorating and/or treating a HEV infection, which can include administering to a subject in need thereof an effective amount of one or more compounds and/or a pharmaceutically acceptable salt thereof as described herein, or a pharmaceutical composition that includes one or more compounds and/or a pharmaceutically acceptable salt thereof as described herein, wherein the compounds and their pharmaceutically acceptable salts described herein can be of Formula (I), or a pharmaceutically acceptable salt thereof.

Other embodiments described herein relate to a compound and/or a pharmaceutically acceptable salt thereof as described herein, for use in ameliorating or treating a HEV infection, or a pharmaceutical composition for use in ameliorating or treating a HEV infection as described herein that includes one or more compounds and/or a pharmaceutically acceptable salt thereof as described herein, wherein the compounds and their pharmaceutically acceptable salts described herein can be of Formula (I), or a pharmaceutically acceptable salt thereof.

Other embodiments described herein relate to a method of inhibiting viral replication of a HEV, which can include contacting a cell infected with the HEV with an effective amount of a compound described herein (e.g., of Formula (I), or a pharmaceutically acceptable salt thereof), and/or a pharmaceutical composition that includes one or more compounds described herein (e.g., a compound of Formula (I), or a pharmaceutically acceptable salt thereof). In an embodiment, the method of inhibiting viral replication of a HEV is an in vitro method.

In some embodiments, an effective amount of one or more compounds described herein (e.g., a compound of Formula (I), or a pharmaceutically acceptable salt thereof), and/or a pharmaceutical composition that includes one or more compounds described herein (e.g., a compound of Formula (I), or a pharmaceutically acceptable salt thereof) can be used to treat ameliorate and/or prevent one more symptoms of an infection caused by a HEV (e.g., by administration to a subject in need thereof). For example, a compound of Formula (I), or a pharmaceutically acceptable salt thereof, can be used to treat, ameliorate and/or prevent one or more of the following symptoms caused by a HEV infection: fever, jaundice, educed appetite (anorexia), nausea, vomiting, abdominal pain, itching, skin rash, and/or joint pain.

In some embodiments, an effective amount of one or more compounds described herein (e.g., a compound of Formula (I), or a pharmaceutically acceptable salt thereof), and/or a pharmaceutical composition that includes one or more compounds described herein (e.g., a compound of Formula (I), or a pharmaceutically acceptable salt thereof) can be used to treat, ameliorate and/or prevent one more conditions related to an infection caused by a HEV (e.g., by administration of an effective amount to a subject in need thereof). For example, in an embodiment, an effective amount of a compound of Formula (I), or a pharmaceutically acceptable salt thereof, can be used to slow or prevent the progression of a HEV infection to a chronic HEV infection in a subject to which the compound or salt is administered. In an embodiment, an effective amount of a compound of Formula (I), or a pharmaceutically acceptable salt thereof, can be used to ameliorate or treat a HEV-associated disease or HEV-induced disease (e.g., a chronic HEV-induced disease) in a subject to which the compound or salt is administered. In an embodiment, an effective amount of a compound of Formula (I), or a pharmaceutically acceptable salt thereof, can be used to slow or prevent the aggravation of a HEV-associated disease or HEV-induced disease (e.g., chronic HEV-induced disease) in a subject to which the compound or salt is administered. Examples of such HEV-associated diseases or HEV-induced (chronic) diseases include acute pancreatitis, fulminant liver failure, Guillain-Barré syndrome, neuralgic amyotrophy, hemolytic anemia (e.g., in a subject with G6PD deficiency), glomerulonephritis, glomerulonephritis with nephrotic syndrome, cryoglobulinemia, mixed cryoglobulinemia, and/or thrombocytopenia.

In some embodiments, an effective amount of one or more compounds described herein (e.g., a compound of Formula (I), or a pharmaceutically acceptable salt thereof), and/or a pharmaceutical composition that includes one or more compounds described herein (e.g., a compound of Formula (I), or a pharmaceutically acceptable salt thereof) can be used to treat, ameliorate and/or prevent one more fibrotic or fibrotic-related conditions that are related to an infection caused by a HEV (e.g., by administration of an effective amount to a subject in need thereof). In an embodiment, an effective amount of a compound of Formula (I), or a pharmaceutically acceptable salt thereof, can be used to ameliorate (e.g., slow or prevent the progression of) a stage of fibrosis in a subject having an HEV infection to which the compound or salt is administered. For example, an effective amount of a compound of Formula (I), or a pharmaceutically acceptable salt thereof, can be used to ameliorate the extent of liver damage in a subject having an HEV infection to which the compound or salt is administered, wherein the liver damage is caused or aggravated by HEV infection (including chronic HEV infection). In another embodiment, an effective amount of a compound of Formula (I), or a pharmaceutically acceptable salt thereof, can be used to ameliorate fibrosis (e.g., slow or prevent the progression of fibrosis) in a subject having an HEV infection to which the compound or salt is administered. For example, in an embodiment, an effective amount of a compound of Formula (I), or a pharmaceutically acceptable salt thereof, can be used to prevent cirrhosis (e.g., slow or prevent the progression of an earlier stage of liver fibrosis to a cirrhotic stage) in a subject having an HEV infection (including chronic HEV infection) to which the compound or salt is administered.

In some embodiments, the particular characteristics of a subject are taken into consideration when using a compound (or pharmaceutically acceptable salt thereof) or carrying out a method as described herein. In addition to being identified as a subject in need of treatment for a condition as described herein (such as a HEV infection), a subject can also be identified on the basis of a particular characteristic that results in vulnerability to HEV infection or its effects. For example, in an embodiment, the subject has hemolytic anemia and also has the hereditary risk factor glucose-6-phosphate dehydrogenase deficiency (G6PD deficiency). In various embodiments the subject can be in need of treatment for a condition as described herein (such as a HEV infection) and also a pregnant woman, an immuno-compromised subject, an immuno-deficient subject and/or organ transplant patient. Thus, any of the compound or salt administration steps of the methods described herein can be conducted in conjunction with a step of identifying one or more clinically relevant characteristics of the subject. For example, an embodiment provides a method of ameliorating or treating a Hepatitis E (HEV) infection comprising identifying a pregnant woman subject in need thereof and administering to the subject an amount of a compound of Formula (I), or a pharmaceutically acceptable salt thereof that is effective to treat the HEV infection and thereby prevent or slow progression to fulminant liver failure.

In some embodiments, the particular characteristics of the HEV are taken into consideration when using a compound (or pharmaceutically acceptable salt thereof) or carrying out a method as described herein. For example, as noted above, HEV can be genotype 1, genotype 2, genotype 3, or genotype 4, with various known subtypes. In addition to being identified as a subject in need of treatment for a condition as described herein (such as a HEV infection), a subject can also be identified on the basis of a particular characteristic of the HEV itself, such as genotype.

In some embodiments, the particular characteristics of the compound (or salt) described herein are taken into consideration when using the compound or carrying out a method as described herein. For example, the compounds of Formula (I), and their pharmaceutically acceptable salts can have various potencies. In an embodiment, a compound of Formula (I), or a pharmaceutically acceptable salt thereof, has an $EC_{50}$ of 0.30 μM or less; an $EC_{50}$ of 0.25 μM or less, an $EC_{50}$ of 0.20 μM or less; or an $EC_{50}$ μM of 0.15 or less. In an embodiment, a compound of Formula (I), or a pharmaceutically acceptable salt thereof, has an $EC_{50}$ of about 1.3 μM or less; an $EC_{50}$ of about 1.20 μM or less, an $EC_{50}$ of about 0.9 μM or less; or an $EC_{50}$ μM of about 0.75 or less. Potency data for exemplified embodiments of compounds of Formula (I) are provided in the Examples below. The application relates more particularly to those compounds as defined herein which show an $EC_{50}$ of less than 0.30 μM (more particularly of 0.25 μM or less, or of 0.20 μM or less, or of 0.15 μM or less) for the inhibition of HEV DNA for example in the Huh7 cell line (e.g., as described in example 2 below), more particularly an $EC_{50}$ of less than 0.30 μM (more particularly of 0.25 μM or less, or of 0.20 μM or less, or of 0.15 μM or less) for the inhibition of HEV DNA when measured 3 days after the compound has been placed in the Huh7 cell culture (eg as described in example 2 below). As used herein, the half maximal effective concentration (EC50) is intended in accordance with its general meaning in the field. It may more particularly refer to the concentration of a compound which induces a response halfway between the baseline and maximum, typically after a specified exposure time. The EC50 value is commonly used as a measure of a compound's potency, with a lower value generally indicating a higher potency.

Various indicators for determining the effectiveness of a method for treating a viral infection, such as a HEV infection, are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

Compounds of the application may also be useful for treating or ameliorating viral infection(s) other than a HEV infection, for example in treatment of one or more infection (s) selected from HBV (chronic) infection, HCV infection and Dengue infection.

In some embodiments, an effective amount of a compound of Formula (I), or a pharmaceutically acceptable salt thereof, is an amount that is effective to reduce viral titers to undetectable levels, for example, to about 1000 to about 5000, to about 500 to about 1000, or to about 100 to about 500 genome copies/mL serum. In some embodiments, an effective amount of a compound of Formula (I), or a pharmaceutically acceptable salt thereof, is an amount that is effective to reduce viral load compared to the viral load before administration of the compound of Formula (I), or a pharmaceutically acceptable salt thereof. In some embodiments, an effective amount of a compound of Formula (I), or a pharmaceutically acceptable salt thereof, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of the compound of Formula (I), or a pharmaceutically acceptable salt thereof. For example, in an embodiment the viral load is measured before administration of the compound of Formula (I), or a pharmaceutically acceptable salt thereof, and again after completion of the treatment regime with the compound of Formula (I), or a pharmaceutically acceptable salt thereof (for example, 1 week after completion). In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of a HEV relative to pre-treatment levels in a subject, as determined after completion of the treatment regime (for example, 1 week after completion). In some embodiments, a compound of Formula (I), or a pharmaceutically acceptable salt thereof, can result in a reduction of the replication of a HEV relative to pre-treatment levels in the range of about 2 to about 5 fold, about 10 to about 20 fold, about 15 to about 40 fold, or about 50 to about 100 fold.

As will be readily apparent to one skilled in the art, the useful in vivo dosage to be administered and the particular mode of administration will vary depending upon the age, weight, the severity of the affliction, and mammalian species treated, the particular compounds or pharmaceutically acceptable salts thereof employed, and the specific use for which these compounds or salts are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively, dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound or pharmaceutically acceptable salt thereof and can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds and pharmaceutically acceptable salts disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.
EXAMPLES
Example 1: Synthesis of Compounds
Compound 1
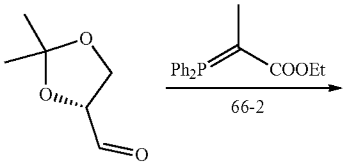
66-1
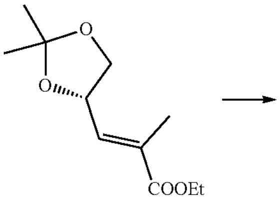
66-3
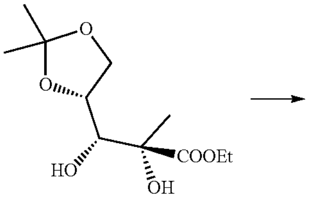
66-4
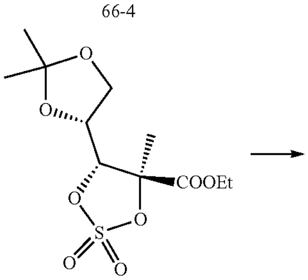
66-5
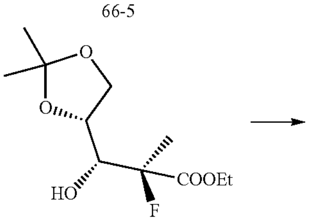
66-6
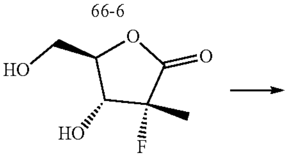
66-7
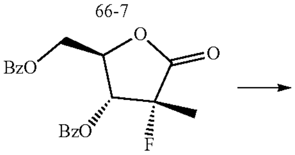
66-8
-continued
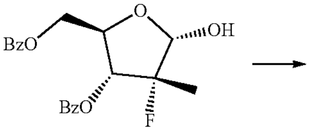
66-9
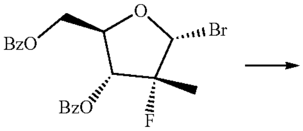
66-10
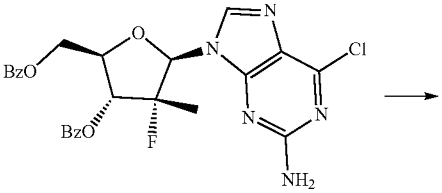
66-11
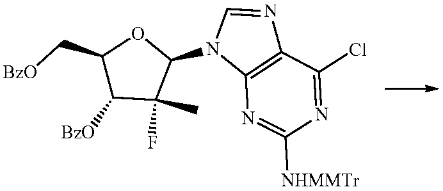
66-12
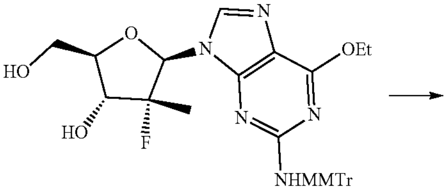
66-13
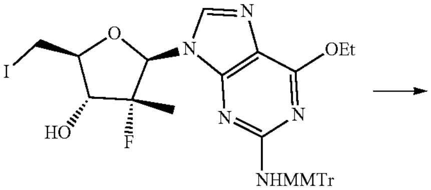
66-14
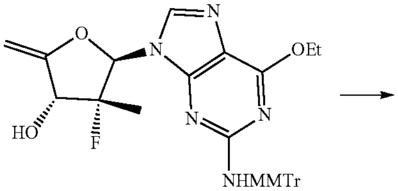
66-15
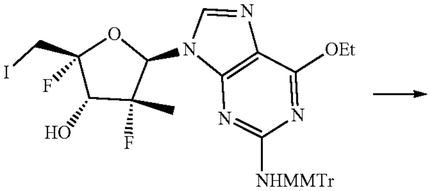
66-16

-continued

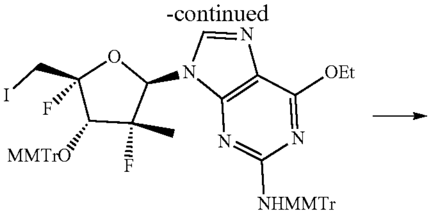

66-17

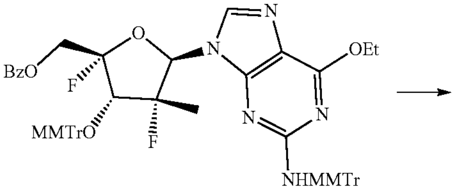

66-18

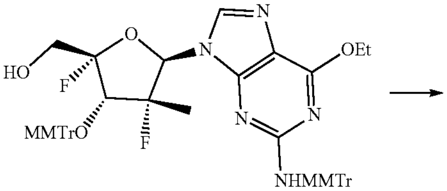

66-19

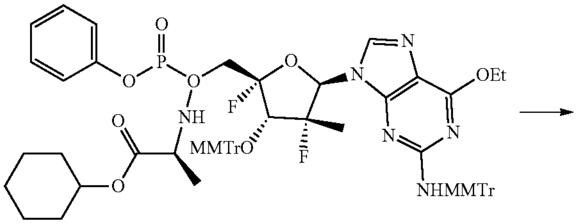

66-20

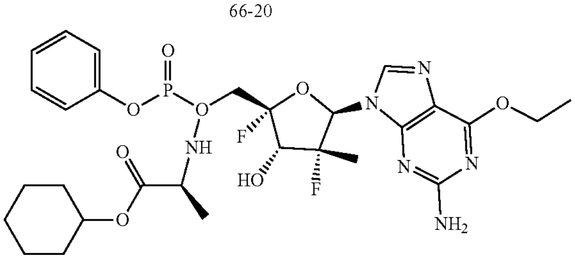

1

Compound 66-2 (2648 g, 7.3 mol) was dissolved in anhydrous dichloromethane (10 L), and the solution was cooled to −40° C. with stirring under $N_2$. Compound 66-1 (1 kg, 7.69 mol) was dissolved in anhydrous CH2CI2 (3 L) and added to the solution of 66-2 over 30 mins at −40° C. The stirred mixture was allowed to warm to R. T. overnight. The mixture was concentrated under reduced pressure to dryness, and the residue was suspended in TMBE (6 L). The suspension was filtered to remove $Ph_3PO$, and the filtrate was concentrated under reduced pressure to afford crude 66-3 (1230 g, 78.6%). $^1H$ NMR (400 Hz) (CDCI3): δ 6.65 (dt, J=7.6 Hz, 1H), 4.82 (dd, J=14.8, 7.6 Hz, 1H), 4.20-4.10 (m, 3H), 3.59 (t, J=8.0 Hz, 1H), 1.86 (d, J=1.2 Hz, 3H), 1.41 (s, 3H), 1.37 (s, 3H), 1.26 (t, J=6.8 Hz, 3H).

Crude 66-3 (1230 g, 5.74 mol) was dissolved in acetone (30 L) at 0-5° C. $KMnO_4$ (1 107 g, 5.17 mol) was added in one portion. After being stirred at 0-5° C. for 5 h, the reaction was quenched with sat. aq. sodium sulfite (20 L). After 30 mins, a colorless suspension was formed. The solid was removed by filtration and washed with EA (6 L). The filtrate was extracted with EA (3×2 L). The combined extracts were dried over $Na_2SO_4$, filtered, and concentrated under reduced pressure to give a white solid residue. The residue was dissolved in EA, and PE was added to give a precipitate. The solid was collected by filtration and recrystallization was performed 3 times to give 66-4 (770 g, 53.6%) as a white solid.

To a stirred solution of 66-4 (770 g, 3.1 mol) in anhydrous DCM (5 L) and triethylamine (1.1 L, 8.05 mol) at 0° C. was added slowly sulfuryl chloride (300 mL, 3.6 mmol). The mixture was stirred at R. T. for 2 h, diluted with DCM (3 L), and washed with sat. $NaHCO_3$ aq. and brine. The organic phase was dried over anhydrous $Na_2SO_4$, filtered, and concentrated under reduced pressure. The residue was purified by a silica gel column using PE:EA=1:0 to 10:1 as the eluent to give 66-5 (490 g, 50.6%) as an oil.

Tetraethylammonium fluoride hydrate (650 g, 3.7 mol) was added into a solution of 66-5 (490 g, 1.6 mol) in anhydrous dioxane (3 L), and the mixture was heated to 120° C. for 16 h. The mixture was then cooled to ambient temperature. 2,2-Dimethoxypropane (3 L) was added followed by cone, aq hydrochloric acid (200 mL). The mixture was stirred for 3 h at ambient temperature. The solvent was concentrated to ½ of the original volume, and then diluted with EA (3 L). The mixture was washed with cold sat. aq. sodium bicarbonate and brine. The combined aqueous layer was back-extracted with EA (1 L). The combined organic layer was dried over anhydrous $Na_2SO_4$, filtered, and concentrated at low pressure to give crude 66-6 (220 g, 70.8%).

Crude 66-6 (220 g, 0.89 mol) was dissolved in ethanol (2 L) and cone. aq. HCl (60 mL). The solution was stirred at ambient temperature for 48 h. and then concentrated under reduced pressure followed by co-evaporations with toluene 3 times to give 66-7 as a pale yellow solid (1 10 g).

Compound 66-7 (1 10 g) was dissolved in anhydrous pyridine (1 L). Benzoyl chloride (200 mL, 1.67 mol) was added slowly at 0-5° C. The mixture was stirred at ambient temperature for 45 mins. The reaction was quenched with ice and MeOH to form a precipitate. After filtration, the filtrate was washed with MeOH to give 66-8 (200 g, 61.2%) as a white solid.

To a solution of 66-8 (100 g, 269 mmol) in anhydrous THF (1000 ml) was added dropwise a solution of lithium tri-tert-butoxyaluminohydride (400 ml, 1M, 0.4 mol) at −78° C. under $N_2$ for 30 mins. The solution was stirred at −20° C. for 1 h, and TLC (PE: EA=3 1) showed that the reaction was complete. The mixture was quenched with sat.$NH_4$ Cl, and diluted with EA. After filtration, the filtrate was extracted with EA. The combined layers were dried over $Na_2SO_4$, and concentrated at low pressure. The residue was purified by a silica column gel (PE:EA=20:1) to give 66-9 (100 g, 100%) as a colorless oil.

To a stirred solution of $PPh_3$ (140 g, 382 mol) in $CH_2Cl_2$ (1000 ml) was added 66-9 (100 g, 269 mmol) at −20° C. under N 2. After stirring for 15 mins, $CBr_4$ (177 g, 382 mol) was added dropwise while maintaining the temperature between −25 and −20° C. under $N_2$. The mixture was stirred below −17° C. for 20 mins. Silica gel was added to the mixture. The mixture was filtered through cold silica column gel and washed with PE: EA (50:1 to 4:1). The combined filtrates were concentrated under reduced pressure at R.T. to give the crude oil product. The residue was purified by a silica column gel a second time (PE:EA=50:1 to 4:1) to give 66-10 (a-isomer, 64 g, yield: 55%) as a colorless oil.

A mixture of 6-chloro-guanine (55.8 g, 316.5 mol) and t-BuOK (39.5 g, 352.7 mmol) in t-BuOH (500 mL) and MeCN (280 mL) was stirred for 30 mins. Compound 66-10

(48 g, 105.5 mmol) was added at R.T., and the mixture was heated to 50° C. and stirred overnight. The reaction was monitored by TLC (PE:EA=2:1). The mixture was quenched with solid $NH_4Cl$. After stirring for 1 h, the mixture was filtered and washed with MeCN. The filtrate was evaporated at low pressure, and the residue was purified by a silica gel column to give 66-11 (33 g, 57%).

To a solution of 66-11 (49 g, 93.1 mol) in $CH_2Cl_2$ (200 mL) was added $AgNO_3$ (31.7 g, 186 mmol), collidine (22.5 g, 186 mmol) and MMTrCl (43 g, 140 mmol) in small portions under $N_2$ at 0° C. The mixture was stirred at R.T., and monitored by TLC (PE:EA=4:1). After filtration, the organic phase was washed with $NaHCO_3$ aqueous and brine. The organic layer was dried over anhydrous $Na_2SO_4$and concentrated at low pressure. The residue was purified by a silica gel column (PE:ME=20:1 to 1:1) to give 66-12 (70 g, 94.2%).

Sodium (10.1 g, 439 mmol) was dissolved in dry EtOH (600 mL) at 70° C. and then cooled to 0° C. To a solution of 66-12 (70 g, 87.7 mmol) was added a freshly prepared NaOEt solution in portions at 0° C., and the mixture was stirred for 1 h. at R.T. After TLC and LCMS showed the reaction was completed, the reaction was quenched with carbon dioxide. The mixture was evaporated at low pressure, and the residue was purified using silica gel column chromatography (DCM:MeOH=100:1 to 20:1) to give 66-13 (50 g, yield 5%) as a yellow solid.

A mixture of $PPh_3$ (35 g, 133.5 mol) and 12 (31.75 g, 125 mmol) in anhydrous pyridine (600 mL) was stirred for 30 mins, and then a solution of 66-13 (50 g, 83.3 mmol) in pyridine (100 mL) was added at 0° C. The mixture was stirred overnight at R.T. and monitored by TLC (DCM: MeOH=50:1). The reaction was quenched with a sat. $NaHCO_3$ solution, and extracted with DCM (3×50 mL). The organic phase was dried over anhydrous $MgSO_4$, and evaporated at low pressure. The residue was purified using silica gel column chromatography (DCM:MeOH=200:1 to 50:1) to give 66-14 (50 g, 84.7%).

To a solution of 66-14 (37 g, 52.1 mmol) in dry THF (400 mL) was added DBU (16 g, 105 mmol). The mixture was heated to reflux and stirred for 3 h. The reaction was monitored by LCMS. The reaction was quenched with a sat. $NaHCO_3$ solution, and extracted with EA. The combined organic layers were dried over anhydrous $Na_2SO_4$, and evaporated at low pressure. The residue was purified using silica gel column chromatography (PE:EA=10:1 to 5:1) to give 66-15 (25 g, 61.1%) as a white solid.

To an ice-cold solution of 66-15 (26 g, 44.6 mmol) in dry MeCN (300 mL) was added NIS (12.68 g, 56 mmol) and $NEt_3{\cdot}3HF$ (10.6 g, 67 mmol) at 0° C. The reaction was stirred at R.T. for 2 h. and monitored by LCMS. After the reaction was completed, the reaction was quenched with a sat $Na_2SO_3$ and sat. $NaHCO_3$ solution, and extracted with EA. The organic layer was separated, dried over anhydrous $Na_2SO_4$, and evaporated at low pressure. The residue was purified using silica gel column chromatography (PE: EA=8:1 to 1:1) to give 66-16 (21 g, 64.4%) as a white solid.

To a solution of 66-16 (21 g, 28.8 mol) in $CH_2Cl_2$ (150 mL) was added $AgNO_3$ (9.8 g, 59.6 mmol) and collidine (7 g, 59.8 mmol) and MMTrCl (13.1 g, 42.5 mmol) in small portions under $N_2$ at 0° C. The mixture was stirred at R.T., and the reaction was monitored by TLC (PE:EA=2:1). After filtration, the solution was washed with sat. aq. $NaHCO_3$ and brine. The organic layer was separated, dried over anhydrous $Na_2SO_4$ and concentrated at low pressure. The residue was purified by a silica gel column to give 66-17 (25 g, yield 86.5%).

To a solution of 66-17 (22 g, 22 mmol) in dry DMF (500 mL) was added NaOBz (31.9 g, 220 mmol) and 15-crown-5 (48.4 g, 220 mmol), and the mixture was stirred for 72 h. at 95° C. The mixture was diluted with EA, washed with water and brine, and dried over $MgSO_4$. The organic layer was evaporated at low pressure, and the residue was purified using a silica gel column chromatography to give 66-18 (15 g, 68.8%) as a white solid.

Compound 66-18 (15.2 g, 15.3 mmol) was co-evaporated with anhydrous toluene 3 times to remove FLO. The compound was treated with $NH_3$ in MeOH (7 N, 200 mL) at R.T. The mixture was stirred for 18 h at R.T., and the reaction was monitored by LCMS. The residue was concentrated at low pressure, and purified using silica gel column chromatography to give 66-19 (11 g, 81%) as a white solid.

To a stirred solution of 66-20 (14 g, 15.73 mmol) in anhydrous $CH_3CN$ (150 mL) was added N-methylimidazole (23.5 g, 283.9 mmol) at 0 to 5° C. (ice/water bath) followed by a solution of phenyl(cyclohexanoxy-L-alaninyl)phosphorochloridate (16.33 g, 47.2 mmol, dissolved in 50 mL of $CH_3CN$). The solution was stirred at 0 to 5° C. for 12 h and then diluted with EA. The solution was washed with 50% aqueous citric acid solution and brine. The organic layer was separated, dried over anhydrous $MgSO_4$ and filtered. The filtrate was concentrated at low pressure, and the residue was purified on silica gel with PE:EA=5:1 as the eluent to give 66-20 (17.62 g, 93.4%) as a white solid.

Compound 66-20 (17.62 g, 14.7 mmol) was dissolved in 80% AcOH (200 mL), and the mixture was stirred overnight at R.T. After removal of the solvents, the reside was purified on silica gel using PE:EA=2:1 as eluent to give the crude product, which was purified on via reverse-phase HPLC using acetonitrile and water to give compound 1 (5.25 g, yield 66%) as a white solid. ESI-LCMS: m/z 655 $[M+H]^+$.

Compound 2

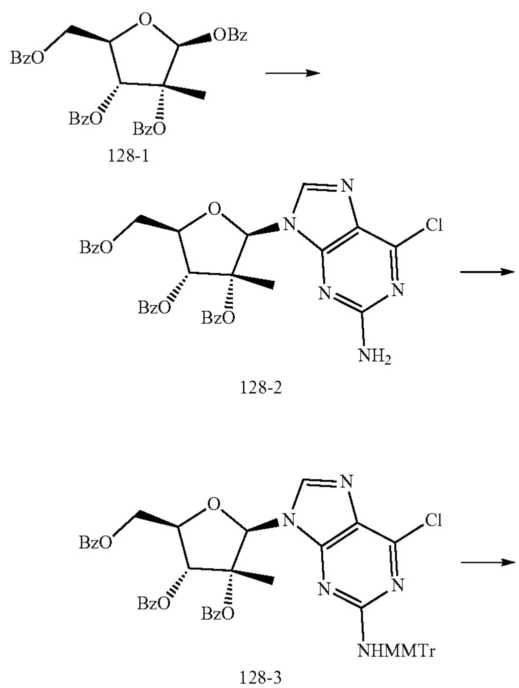

128-1

128-2

128-3

-continued

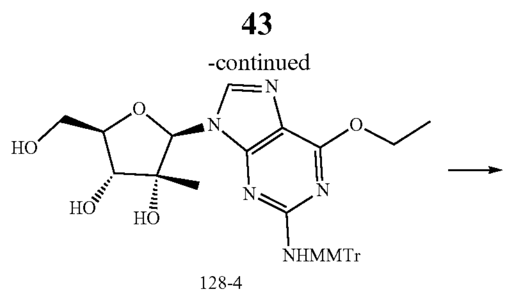

128-4

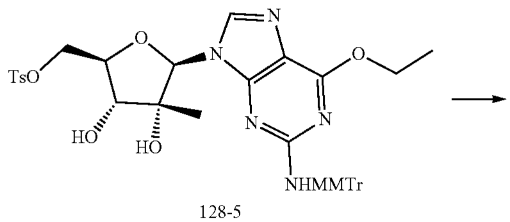

128-5

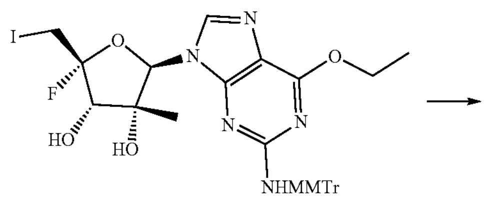

128-6

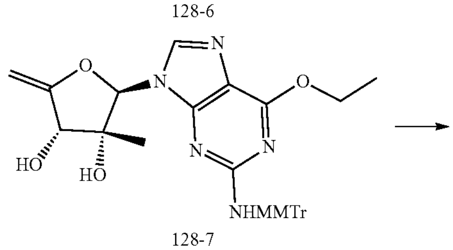

128-7

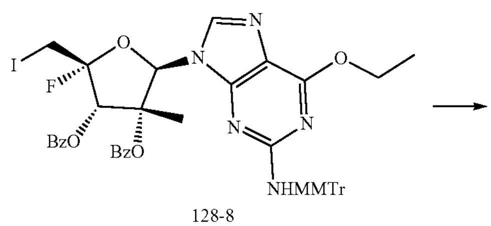

128-8

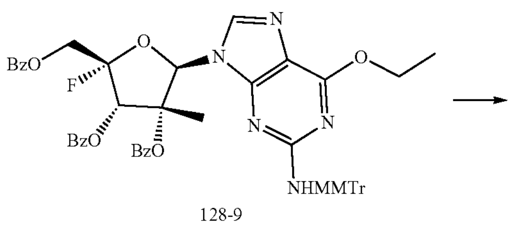

128-9

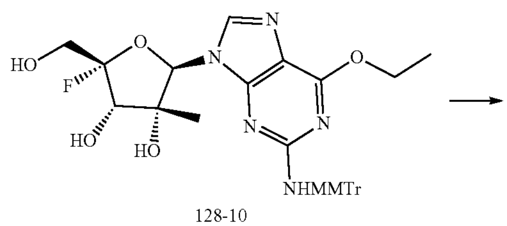

128-10

-continued

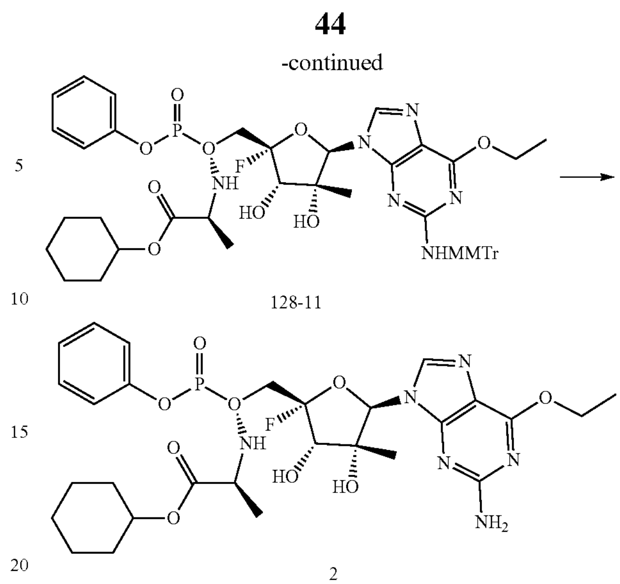

128-11

2

Compound 128-1 (50 g, 86.0 mmol) and 6-Cl-guanine (16.1 g, 98.2 mmol) were co-evaporated with anhydrous toluene 3 times. To a solution of 128-1 in MeCN (200 mL) was added DBU (39.5 g, 258.0 mmol) at 0° C. The mixture was stirred at 0° C. for 30 mins, and then TMSOTf (95.5 g, 430.0 mmol) was added dropwise at 0° C. The mixture was stirred at 0° C. for 30 mins. The mixture was heated to 70° C., and stirred overnight. The solution was cooled to RT and diluted with EA (100 mL). The solution was washed with sat. $NaHCO_3$ solution and brine. The organic layer was dried over $Na_2SO_4$, and concentrated at low pressure. The residue was purified by column on silica gel (EA in PE from 10% to 40%) to give 128-2 (48.0 g, yield: 88.7%) as a yellow foam. ESI-MS: m/z 628 $[M+H]^+$.

To a solution of 128-2 (48.0 g, 76.4 mol), $AgNO_3$ (50.0 g, 294.1 mmol) and collidine (40 mL) in anhydrous DCM (200 mL) was added MMTrCl (46.0 g, 149.2 mmol) in small portions under $N_2$. The mixture was stirred at RT for 3 h under $N_2$. The reaction was monitored by TLC. The mixture was filtered, and the filter was washed with sat. $NaHCO_3$ solution and brine. The organic layer was dried over anhydrous $Na_2SO_4$, and concentrated at low pressure. The residue was purified by silica gel column (EA in PE from 5% to 50%) to the give crude 128-3 (68 g, 98%). ESI-MS: m/z 900.1 $[M+H]^+$.

Sodium (8.7 g, 378.0 mmol) was dissolved in dry EtOH (100 mL) at 0° C., and slowly warmed to RT. Compound 128-3 (68.0 g, 75.6 mmol) was treated with freshly prepared NaOEt solution, and stirred overnight at RT. The reaction was monitored by TLC, and the mixture was concentrated at low pressure. The mixture was diluted with $H_2O$ (100 mL), and extracted with EA (3×100 mL). The organic layer was dried over anhydrous $Na_2SO_4$, and evaporated at low pressure. The residue was purified by silica gel column chromatography (MeOH in DCM from 1% to 5%) to give 128-4 (34.0 g, 75.2%) as a yellow solid. ESI-MS: m/z 598 $[M+H]^+$.

Compound 128-4 (32.0 g, 53.5 mmol) was co-evaporated with anhydrous pyridine 3 times. To an ice cooled solution of 128-4 in anhydrous pyridine (100 mL) was added TsCl (1 1.2 g, 58.9 mmol) in pyridine (50 mL) dropwise at 0° C. The mixture was stirred for 18 h. at 0° C. The reaction was checked by LCMS (about 70% was the desired product). The reaction was quenched with $H_2O$, and the solution was concentrated at low pressure. The residue was dissolved in EA (100 mL), and washed with sat. $NaHCO_3$ solution. The organic layer was dried over anhydrous $Na_2SO_4$; and evaporated at low pressure. The residue was purified by silica gel column chromatography (MeOH in DCM from 1% to 5%) to give crude 128-5 (25.0 g, 62.2%) as a yellow solid. ESI-MS: m/z 752 $[M+H]^+$.

To a solution of 128-5 (23.0 g, 30.6 mmol) in acetone (150 mL) was added NaI (45.9 g, 306.0 mmol) and TBAI (2.0 g), and refluxed overnight. The reaction was monitored by LCMS. After the reaction was complete, the mixture was concentrated at low pressure. The residue was dissolved in EA (100 mL), washed with brine, and dried over anhydrous $Na_2SO_4$ The organic solution was evaporated at low pressure. The residue was purified by silica gel column chromatography (DCM:MeOH=100:1 to 20:1) to give the crude product. To a solution of the crude product in dry THE (200 mL) was added DBU (14.0 g, 91.8 mmol), and heated to 60° C. The mixture was stirred overnight, and checked by LCMS. The reaction was quenched with sat. NaHCO3, and the solution was extracted with EA (100 mL). The organic layer was dried over anhydrous $Na_2SO_4$, and evaporated at low pressure. The residue was purified by silica gel column chromatography (MeOH in DCM from 1% to 5%) to give 128-6 (12.0 g, 67.4%) as a yellow solid. ESI-MS: m/z 580 $[M+H]^+$.

To an ice cooled solution of 128-6 (8.0 g, 13.8 mmol) in dry MeCN (100 mL) was added NIS (3.9 g, 17.2 mmol) and TEA.3HF (3.3 g, 20.7 mmol) at 0° C. The mixture was stirred at RT for 18 h and checked by LCMS. After the reaction was complete, the reaction was quenched with sat $Na_2SO_3$ and sat. $NaHCO_3$ solution. The solution was extracted with EA. The organic layer was dried over anhydrous $Na_2SO_4$, and evaporated at low pressure. The residue was purified by silica gel column chromatography (EA in PE from 10% to 50%) to give 128-7(7.2 g, 72.0%) as a solid. ESI-MS: m/z 726 $[M+H]^+$.

To a solution of crude 128-7 (7.2 g, 9.9 mmol) in dry DCM (100 mL) was added DMAP (3.6 g, 29.8 mmol), and BzCl (2.8 g, 19.8 mmol) at 0° C. The mixture was stirred overnight, and checked by LCMS. The mixture was washed with sat. $NaHCO_3$ solution. The organic layer was dried over anhydrous $Na_2SO_4$, and evaporated at low pressure. The residue was purified by silica gel column chromatography (EA in PE from 10% to 30%) to give 128-8 (8.0 g, 86.4%) as a solid. ESI-MS: m/z 934 $[M+H]^+$.

To a solution of 128-8 (7.5 g, 8.0 mmol) in dry DMF (100 mL) was added NaOBz (11.5 g, 80.0 mmol) and 15-crown-5 (15.6 mL). The mixture was stirred for 36 h. at 90° C. The mixture was diluted with $H_2O$ (100 mL), and extracted with EA (3×150 mL). The organic layer was dried over anhydrous $Na_2SO_4$, and evaporated at low pressure. The residue was purified by silica gel column chromatography (EA in PE from 10% to 30%) to give crude 128-9 (6.0 g, 80.0%) as a solid. ESI-MS: m/z 928 $[M+H]^+$.

Compound 128-9 (4.0 g, 4.3 mmol) was co-evaporated with anhydrous toluene 3 times, and treated with $NH_3$/MeOH (50 mL, 4N) at RT. The mixture was stirred for 18 h at RT. The reaction was monitored by LCMS, and the mixture was concentrated at low pressure. The residue was purified by silica gel column chromatography (EA in PE from 30% to 50%) to give 128-10 (1.9 g, 71.7%) as a solid. ESI-MS: m/z 616 $[M+H]^+$.

Compound 128-10 (300.0 mg, 0.49 mmol) was co-evaporated with anhydrous toluene 3 times, and was dissolved in MeCN (2 mL). The mixture was treated with NMI (120.5 mg, 1.47 mmol) and the phosphorochloridate reagent (338.1 mg, 0.98 mmol) in MeCN (1 mL) at 0° C. The mixture was stirred for 18 h at RT. The reaction was monitored by LCMS. The mixture was diluted with 10% $NaHCO_3$ solution, and extracted with EA. The residue was purified by silica gel column chromatography (EA in PE from 30% to 50%) to give 128-11 (240 mg, 53.3%) as a solid. ESI-MS: m/z 925 $[M+H]^+$.

Compound 128-11 (240.0 mg, 0.26 mmol) was treated with 80% AcOH (10 mL), and the mixture was stirred for 18 h at RT. The reaction was monitored by LCMS. The mixture was concentrated at low pressure. The residue was purified by silica gel column chromatography (MeOH in DCM from 1% to 3%) to give compound 2 (87.6 mg, 51.7%) as a solid. ESI-MS: m/z 653 $[M+H]^+$.

Compound 3

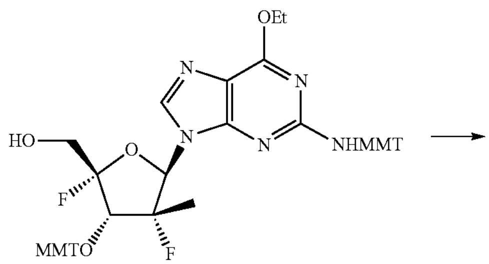

188-1

-continued

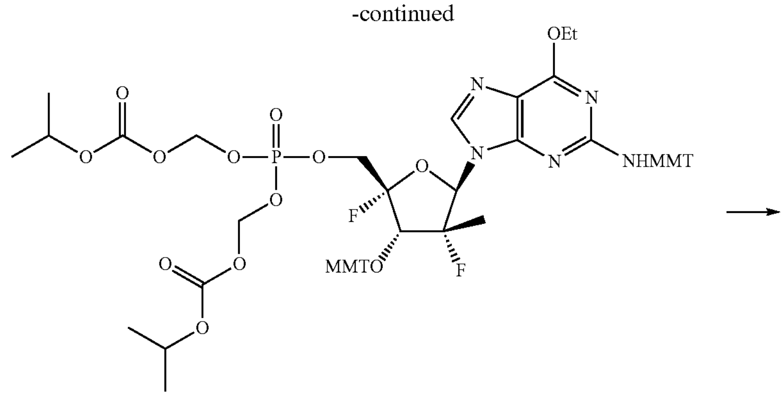

188-2

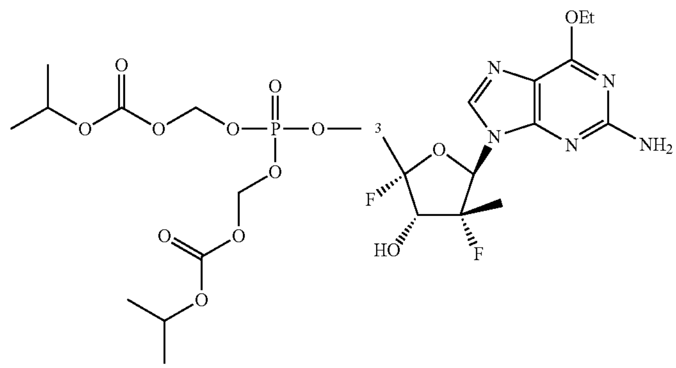

3

Compound 188-2 (70 mg, 58%) was prepared in the same manner from compound 188-1 (90 mg; 0.1 mmol) and triethylammonium bis(isopropyloxycarbonyloxymethyl) phosphate (0.2 mmol) with DIPEA (87 μL), BopCl (44 mg), and 3-nitro-1,2,4-triazole (29 mg) in THF (2 mL) as described in the preparation of compound 156a. Purification was done with hexanes/EtOAc with a 20-80% gradient.

Compound 3 (25 mg, 64%) was prepared from 188-2 (70 mg) in acetonitrile (0.6 mL) and 4 N HCl/dioxane (50 μl) as described in the preparation of 209a below. MS: m/z=658 [M+1].

Compound 4

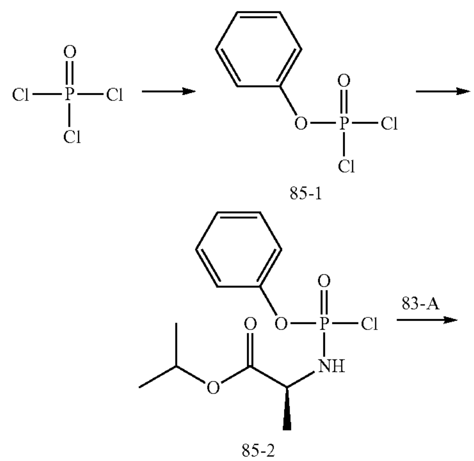

85-1

85-2

-continued

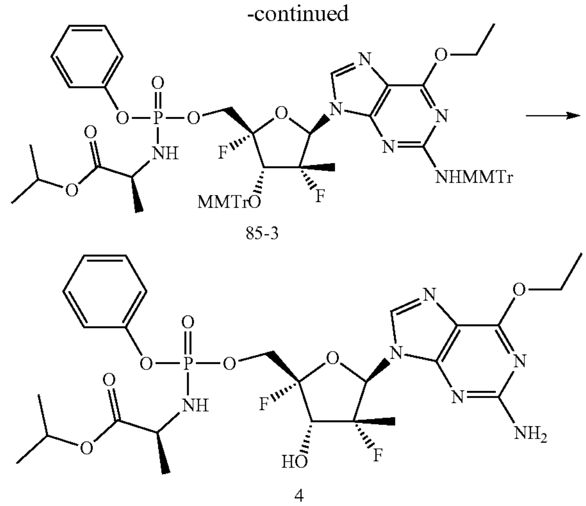

85-3

4

To a stirred solution of $POCl_3$ (2.0 g, 13 mmol) in anhydrous DCM (10 mL) was added phenol (1.22 g, 13 mmol) at −70° C. and TEA (1.31 g, 13 mmol) in DCM (3 mL) dropwise at −70° C. The mixture was gradually warmed to R.T. and stirred for 1 h. A crude solution of 85-1 was obtained.

Compound 85 was prepared using a similar procedure as for the preparation of compound 84 using 85-2 (205 mg, 0.674 mol, in DCM (5 mL) obtained from (S)-isopropyl 2-aminopropanoate hydrochloride and 85-1) and 83-A (300 mg, 0.337 mmol). Compound 4 (50 mg, 74%) was obtained as a white solid. ESI-MS: m/z 615.2 $[M+H]^+$.

Compound 5

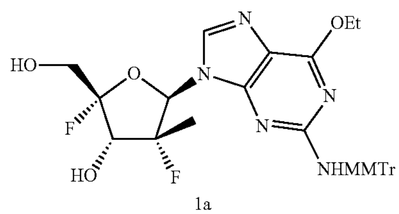

1a

+

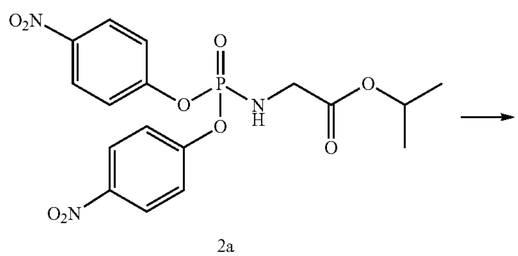

2a

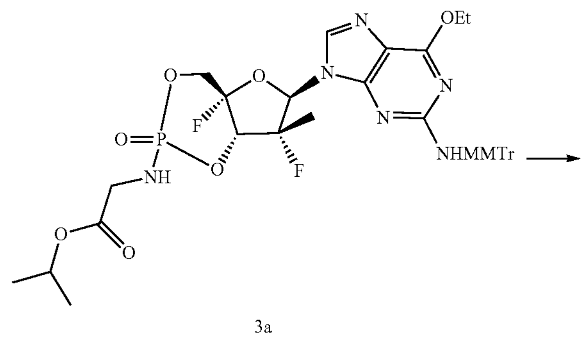

3a

-continued

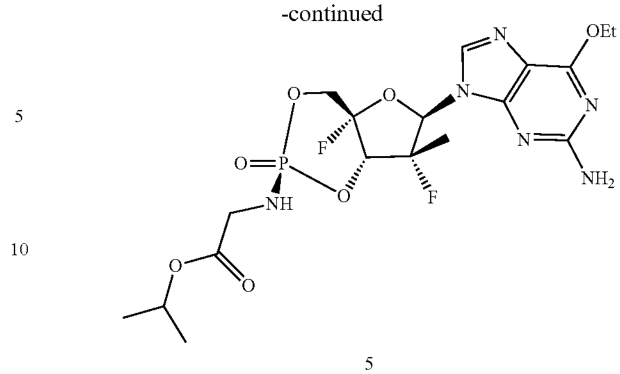

5

A mixture of guanosine analogue 1a (310 mg, 0.5 mmol) in MeCN (15 mL) and DBU (150 μl, 1 mmol) was stirred at rt for 10 min. Then a solution of phosphoramidate 2a (0.44 g, 1 mmol; which can be prepared as described Bioorg. Med. Chem. Lett. 2012, vol. 22, p. 4497-5001) in MeCN (10 mL) was added dropwise and the reaction mixture stirred at rt for 1 h.

Reaction was quenched with 1 N citric acid and diluted with EtOAc. Layers were separated and organic layer was washed with water, sat aq. $NaHCO_3$, brine, and dried ($Na_2SO_4$). Evaporated residue was purified by flash chromatography on silica (35-100% EtOAc in hexanes) to yield 3a (as a mixture of diastereoisomers. A mixture of 3a in 0.04 N solution of HCl in MeCN (3.3 mL) was stirred at rt for 1 h. Reaction was quenched with MeOH and the mixture concentrated. Residue was coevaporated with toluene and MeCN and purified by flash chromatography on silica with 4-20% i-PrOH in $CH_2Cl_2$. Diastereomeric mixture was separated by RP-HPLC (30-100% B, A=0.1% aq. HCOOH, B=0.1% HCOOH in MeCN) to yield 35 mg (14%, for 2 steps) of the target compound 5.

$^1$H-NMR ($CD_3OD$): δ 7.94 (s, 1H), 6.61 (d, J=17.2 Hz, 1H), 6.1 (br, 1H), 5.01 (m, 1H), 4.75 (dd, J=10.8 Hz, 29.3 Hz, 1H), 4.50-4.58 (m, 3H), 3.68 (d, J=14.8 Hz, 2H), 1.41 (t, J=6.8 Hz, 3H), 1.38 (d, J=21.2 Hz, 3H), 1.25 (d, J=6.8 Hz, 6H). $^{31}$P-NMR ($CD_3OD$): δ 7.01. MS, m/z 507.0 $(M+1)^+$.

Preparation of Compound 1a 9-(2-Deoxy-2,4-difluoro-2-C-methyl-β-D-ribofuranosyl)-6-ethoxy-2-(monomethoxytritylamino)purine (1a)

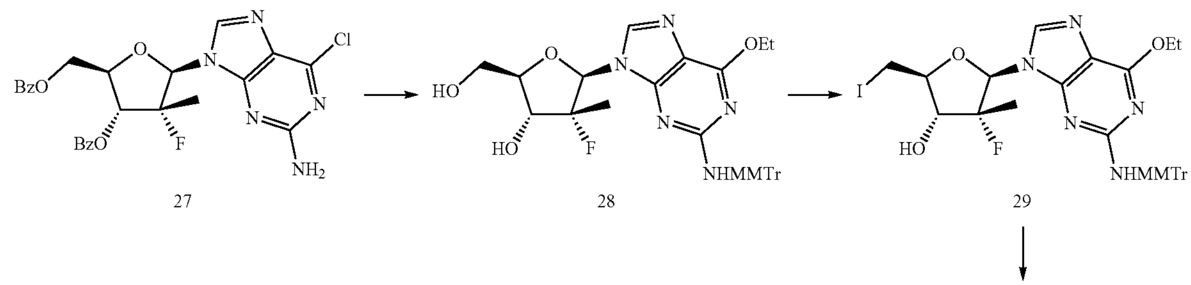

27

28

29

-continued

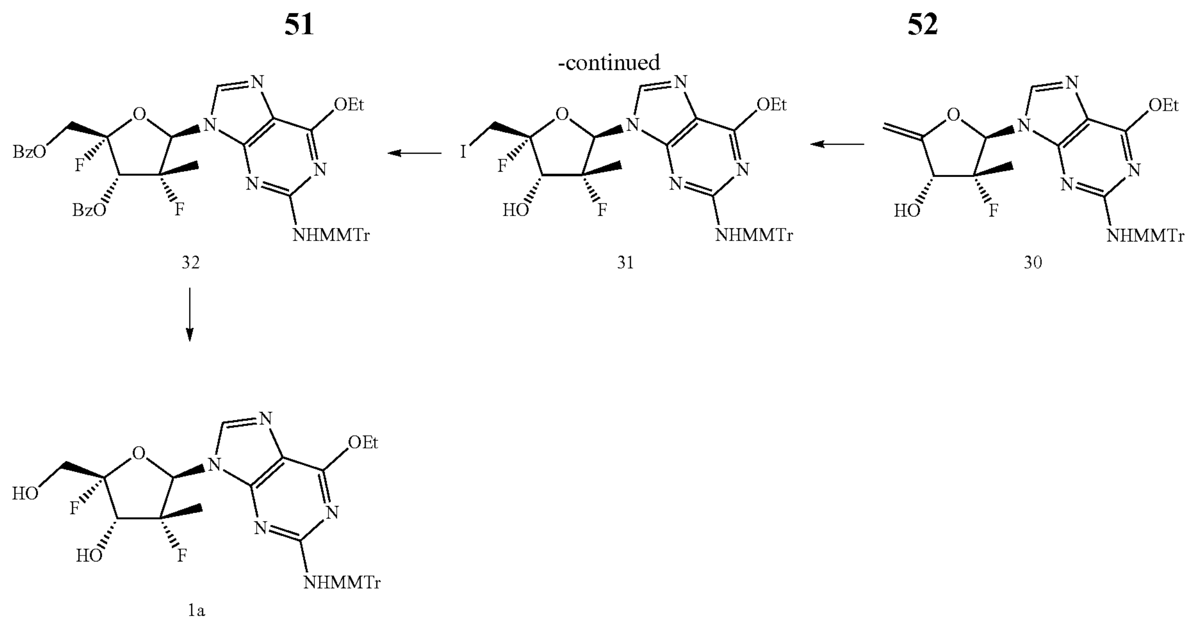

32 31 30

1a 9-(2-Deoxy-2-fluoro-2-C-methyl-β-D-ribofuranosyl)-6-ethoxy-2-(monomethoxytritylamino) purine (28). To a solution of compound 27 (12.5 g, 23.8 mmol) in 50 mL of DCM was added $AgNO_3$ (8.1 g, 47.6 mmol), collidine (5.77 g, 47.6 mmol) and MMTrCl (11 g, 35.6 mmol). Reaction mixture was kept at rt overnight, quenched with methanol and filtered. Solvents were evaporated, the residue purified by column chromatography in 5% MeOH in DCM to get 16 g (84%) of N-tritylated nucleoside. This product in 150 mL of ethanol was treated with NaOEt (50 mL, 2N in ethanol) at 0° C. Reaction was left at rt for 1 h, pH was adjected to 7 with concentrated solution of NH4Cl. Product was extracted with EtOAc and residue purified by column chromatography in 5% MeOH in DCM to get 10.9 g (98%) of nucleoside 28. MS, m/z $(M+H)^+$600. $^1$H-NMR (DMSO-$d_6$): δ 8.13 (s, 1H), 7.51 (s, 1H), 7.15-7.30 (m 13H), 6.80 (m, 2H), 5.61 (d, J=7.2 Hz, 1H), 5.25 (t, J=5.0 Hz, 1H), 4.05 (br, 2H), 3.80 (m, 2H), 3.68 (s, 3H), 3.61 (m, 1H) 1.15 (br, 3H), 0.75 (br, 3H). MS, m/z 600.5 $(M+1)^+$.

9-(2,5-Dideoxy-2-fluoro-2-C-methyl-5-iodo-β-D-ribofuranosyl)-6-ethoxy-2-(monomethoxytritylamino)purine (29). Nucleoside 28 (10 g, 16.5 mmol), triphenylphosphine (5.4 g, 20.6 mmol) and imidazole (1.6 g, 24.7 mmol) were suspended in 30 mL of dry THE and cooled to 10° C. Solution of iodine (5 g, 20 mmol) in dry THF (20 ml) was added and reaction mixture was stirred at room temperature for 5 h. Reaction mixture was quenched with solution of $Na_2S_2O_3$ and diluted with EtOAc. The organic layer was washed with brine, dried over anhydrous sodium sulfate and concentrated under reduced pressure. The residue purified by column chromatography in 2% MeOH in DCM to get 8.9 g (75%) of nucleoside 29 as yellow solid. MS, m/z $(M+H)^+$ 710.

9-(4,5-Didehydro-2,5-dideoxy-2-fluoro-2-C-methyl-β-D-ribofuranosyl)-6-ethoxy-2-(monomethoxytritylamino)purine (30). To a solution of compound 29 (8 g, 11.3 mmol) in 40 mL of THF was added DBU (2.5 ml, 17 mmol) and the mixture was heated at 70-75° C. for 3 h. Reaction was quenched 1M solution of citric acid, organic layer was washed with brine, dried and evaporated. The residue purified by column chromatography in 20% EtOH in hexane to get 2.4 g (37%) of nucleoside 30 as white solid. MS, m/z $(M+H)^+$ 582. $^1$H-NMR ($CDCl_3$): δ 7.42 (s, 1H), 7.19-7.29 (m 12H), 6.78 (m, 2H), 6.30 (s, 1H), 5.8 (br, 1H), 4.6, 4.5, 4.3 (3 br, 4H), 3.77 (m, 2H), 3.68 (s, 3H), 3.61 (m, 1H) 1.35 (br, 3H), 0.75 (br, 3H). MS, m/z 582.4 $(M+1)^+$.

9-(2,5-Dideoxy-2,4-difluoro-5-iodo-2-C-methyl-β-D-ribofuranosyl)-6-ethoxy-2-(monomethoxytritylamino)purine (31). To a stirred cold (−0° C.) solution of nucleoside 30 (4.8 g, 8.2 mmol) in DCM (50 mL) was added triethylamine trihydrochloride (2 mL, 12.6 mmol) immediately followed by addition of NIS (2.7 g, 12 mmol). Reaction was allowed to proceed for 2 h at the same temperature and quenched with saturated solutions of $NaHCO_3$ and $Na_2S_2O_3$ (1:1). After usual work-up the crude product was purified by column chromatography in 20% EtOH in hexane to get 3.5 g (60%) of nucleoside 31. MS, m/z $(M+H)^+$ 728.

9-(3,5-di-O-Benzoyl-2-deoxy-2,4-difluoro-2-C-methyl-β-D-ribofuranosyl)-6-ethoxy-2-(monomethoxytritylamino) purine (32). To Nucleoside 31 (2.1 g, 3 mmol) dissolved in 40 mL of pyridine, BzCl (464 mg, 3.3 mmol) was added and reaction mixture was left at rt overnight. After usual work-up and chromatography on silica gel with 20% EtOAc in hexane 2 g of 3'-benzoylated product was obtained. It was dissolved in DMF (60 mL), NaOBz (3.45 g, 24 mmol) and 15-crown-5 (5.31 mg, 24 mmol) were added and reaction mixture was stirred at 100° C. for 48 h. Solvent was evaporated. After usual work-up the crude product was purified by column chromatography in 20% EtOH in hexane to get 1.1 g (45% for 2 steps) of nucleoside 32. MS, m/z $(M+H)^+$ 826.

9-(2-Deoxy-2,4-difluoro-2-C-methyl-β-D-ribofuranosyl)-6-ethoxy-2-(monomethoxytritylamino)purine 1. Benzoylated nucleoside 32 (1 g, 1.2 mmol) was dissolved in n-butylamine (5 mL) and kept at rt overnight. Butylamine was evaporated and the residue was purified by column chromatography in 10% MeOH in DCM to get 0.62 g (85%) of nucleoside 1a. MS, m/z $(M+H)^+$ 618. $^1$H-NMR (DMSO-$d_6$): δ 7.74 (br, 1H), 7.54 (s, 1H), 7.14-7.27 (m 12H), 6.79 (m, 2H), 5.90 (br, 1H), 5.62 (br, 1H), 4.36 (br, 1H), 4.02 (br, 1H), 3.99 (q, J=7.2 Hz, 2H), 3.67 (s, 3H), 3.62 (m, 2H) 1.14 (t, J=7.2 Hz, 3H), 1.0 (br, 3H). MS, m/z 618.1 $(M+1)^+$.

Compound 6
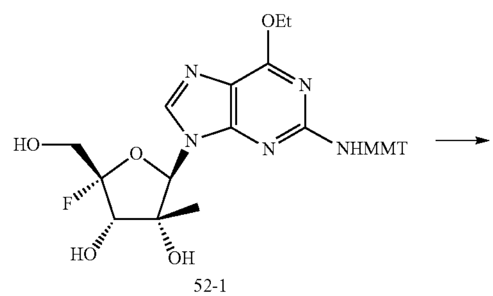
52-1
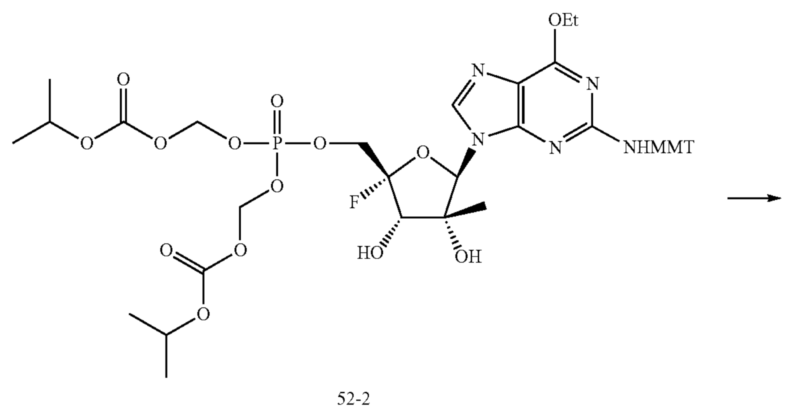
52-2
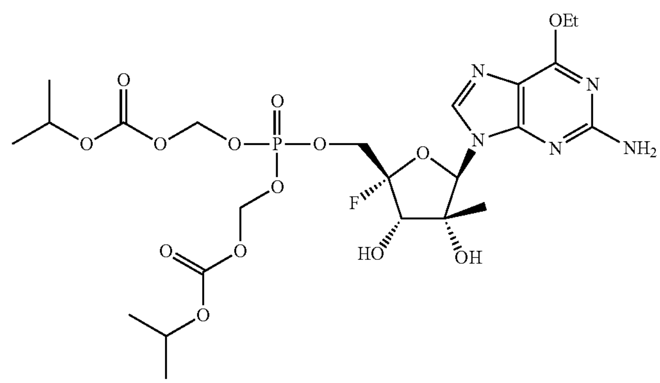
6

Compound 52-2 (158 mg, 50%) was prepared from 52-1 (0.21 g; 0.35 mmol) and triethylammonium bis(isopropyloxycarbonyloxymethyl)phosphate (0.54 mmol) with DIPEA (0.18 mL), BopCl (178 mg), and 3-nitro-1,2,4-triazole (80 mg) in THF (4 mL).

A solution of 52-2 (158 mg) in acetonitrile (1 mL) and HCl (4 N/dioxane; 85 μL) was stirred at R.T. for 30 mins. The reaction was quenched with MeOH and concentrated. The residue was purified on silica gel (10 g column) with $CH_2Cl_2$/i-PrOH (3-10% gradient) to give compound 6 (85 mg, 76%). MS: m/z=656 $[M+1]^+$.

Compound 7

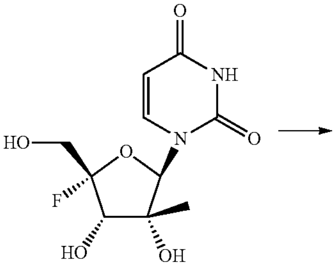

1

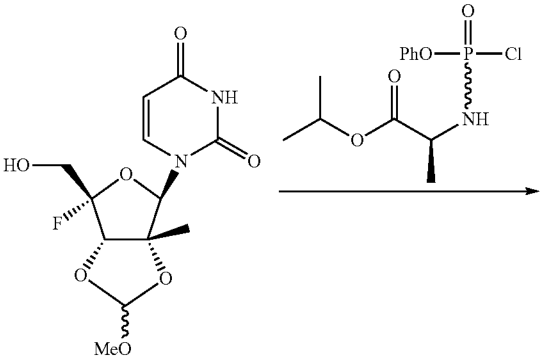

2-1

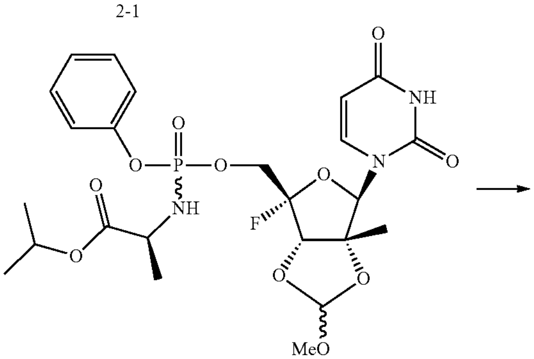

2-2

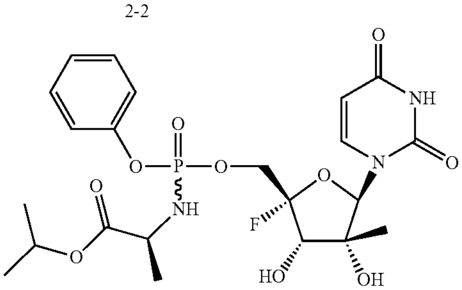

7

To a solution of 1 (1.2 g; 4.3 mmol) in dioxane (30 mL) were added p-toluenesulphonic acid monohydrate (820 mg; 1 eq.) and trimethyl orthoformate (14 mL; 30 eq.). The mixture was stirred overnight at R.T. The mixture was then neutralized with methanolic ammonia and the solvent evaporated. Purification on silica gel column with $CH_2Cl_2$-MeOH solvent system (4-10% gradient) yielded 2-1 (1.18 g, 87%).

To an ice cold solution of 2-1 (0.91 g; 2.9 mmol) in anhydrous THF (20 mL) was added iso-propylmagnesium chloride (2.1 mL; 2 M in THF). The mixture was stirred at 0° C. for 20 mins. A solution of phosphorochloridate reagent (2.2 g; 2.5 eq.) in THF (2 mL) was added dropwise. The mixture was stirred overnight at R.T. The reaction was quenched with saturated aq. NH4Cl solution and stirred at R.T. for 10 mins. The mixture was then diluted with water and $CH_2Cl_2$, and the two layers were separated. The organic layer was washed with water, half saturated aq. $NaHCO_3$ and brine, and dried with $Na_2SO_4$. The evaporated residue was purified on silica gel column with $CH_2$Ci2-iPrOH solvent system (4-10% gradient) to yield Rp/Sp-mixture of 2-2 (1.59 g; 93%).

A mixture of 2-2 (1.45 g; 2.45 mmol) and 80% aq. HCOOH (7 mL) was stirred at R.T. for 1.5 h. The solvent was evaporated and coevaporated with toluene. The obtained residue was dissolved in MeOH, treated with $Et_3N$ (3 drops) and the solvent was evaporated. Purification on silica gel column with $CH_2Cl_2$-MeOH solvent system (4-10% gradient) yielded Rp/Sp-mixture of compound 7 (950 mg; 70%). 31 P-NMR (DMSO-d 6): δ 3.52, 3.47. MS: m/z=544 [M−1]~.

Compound 8

Compound 8 was prepared from guanosine 1a and D-alanine analogue of 2a in similar manner as described for compound 5 (cf. above) in 27% yield (125 mg).

$^1$H-NMR ($CD_3OD$): δ 7.94 (s, 11H), 6.60 (d, J=16.8 Hz, 1H), 6.1 (br, 1H), 4.99 (sept, J=6.4 Hz, 1H), 4.75 (dd, J=10.8 Hz, 29.2 Hz, 1H), 4.48-4.59 (m, 3H), 3.88 (m, 1H), 1.41 (t, J=7.2 Hz, 3H), 1.34-1.40 (m, 6H), 1.25 (d, J=6.4 Hz, 3H), 1.24 (d, J=6.4 Hz, 3H). $^{31}$P-NMR ($CD_3OD$): δ 6.07. MS, m/z 521.0 $(M+1)^+$.

Compound 9

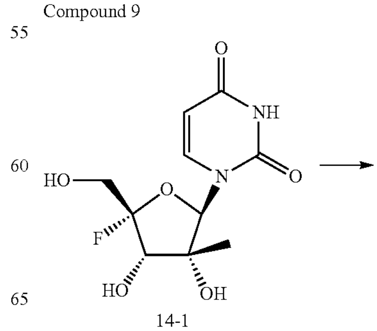

14-1

-continued

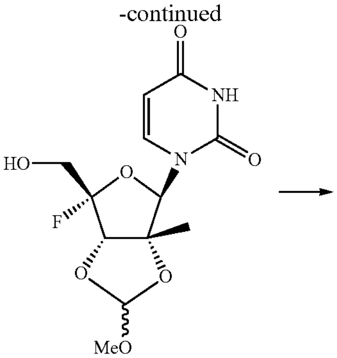

14-2

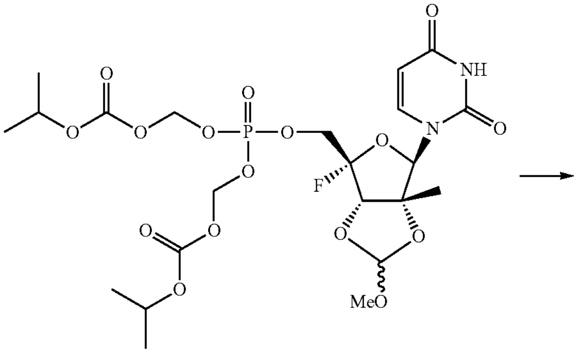

14-3

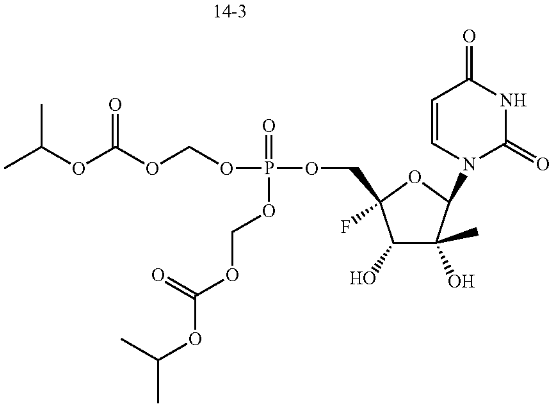

9

A mixture of 14-1 (1.2 g, 4.3 mmol), PTSA monohydrate (0.82 g, 1 eq.), and trimethyl orthoformate (14 mL, 30 eq.) in dioxane (30 mL) was stirred overnight at R.T. The reaction was neutralized with 7 N NH3/MeOH and a white solid removed by filtration. The residue was dissolved in THF (10 mL) and treated with 80% aq. AcOH (5 mL). The mixture was kept at R.T. for 45 mins and then evaporated. The residue was purified on silica gel (25 g column) with $CH_2Cl_2$/MeOH (4-10% gradient) to give 14-2 (1.18 g, 87%).

Compound 14-3 (137 mg, 75%) was prepared from 14-2 (93 mg, 0.29 mmol) and triethylammonium bis(isopropyloxycarbonyloxymethyl)phosphate (0.44 mmol) with DIPEA (0.2 mL), BopCl (147 mg), and 3-nitro-1,2,4-triazole (66 mg) in THF (3 mL). Purification was done with $CH_2Cl_2$/i-PrOH solvent system (3-10% gradient).

A solution of 14-3 (137 mg) in 80% aq. HCOOH was stirred at R.T. for 2 h, and then concentrated. The residue was co-evaporated with toluene and then MeOH containing a small amount of $Et_3N$ (2 drops). Purification on silica (25 g column) with $CH_2Cl_2$/MeOH (4-10% gradient) gave compound 9 (100 mg, 77%). MS: m/z=1175 [2M−1]~.

Compound 10

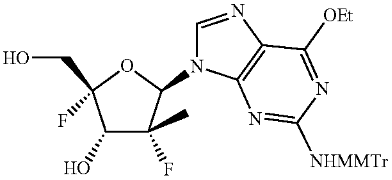

1a

+

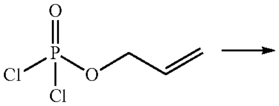

4a

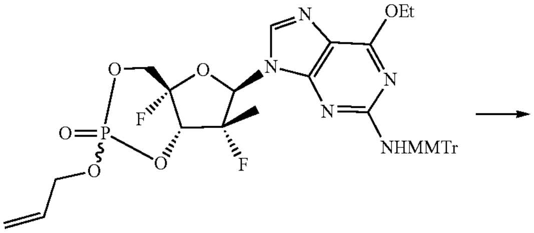

5a

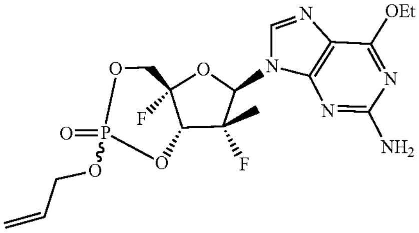

10

Guanosine analogue 1a (185 mg, 0.3 mmol) and tert-BuMgCl (1.2 mL, 1.0 M solution in THF) in anhydrous THF (5 mL) were treated with allyl phosphorodichloridate 4a (72 mg, 0.45 mmol; which can be prepared e.g., as described in Journal of general chemistry of the USSR, 1965, vol. 35, p. 1462-1464. (Zhurnal Obshchei Khimii, 1965, vol. 35, p. 1460-1463). The reaction mixture was stirred at rt for 4 h, quenched with water, and extracted with EtOAc. Organic extract was dried ($Na_2SO_4$), evaporated to dryness and purified on silica gel with gradient of 2-5% MeOH in $CH_2Cl_2$. Protected prodrug 5a (cf. compound 5 above) was dissolved in acetonitrile (5 mL), HCl in dioxane was added (0.5 mL), the mixture kept for 1 h at rt and evaporated. The residue was purified on silica gel with gradient of MeOH in $CH_2Cl_2$ from 2% to 10% to yield the target compound 10 (as a mixture of diastereoisomers (36 mg, 27%)).

$^{31}$P-NMR ($CD_3OD$): δ −5.27, −6.79. MS, m/z 448.2 $(M+1)^+$.

Compound 11

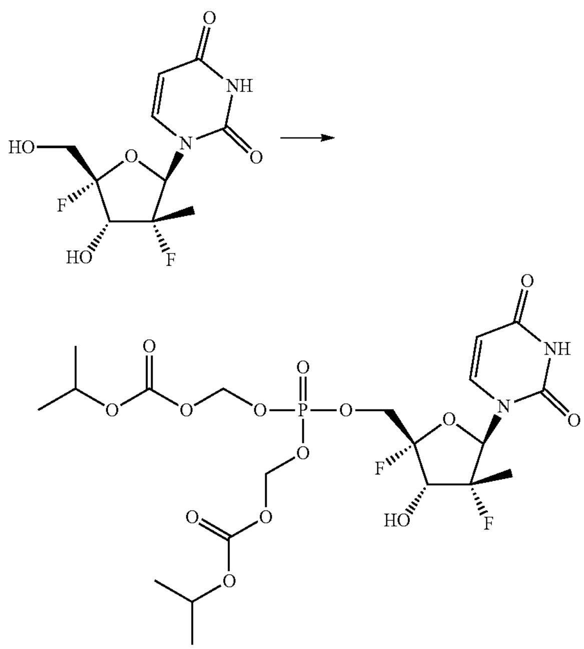

The non-phosphorylated compound in the scheme above (109 mg, 0.39 mmol), and triethylammonium bis(isopropyloxycarbonyloxymethyl)phosphate (0.6 mmol, prepared from 195 mg of bis(isopropyloxycarbonyloxymethyl)phosphate and 85 of Et 3 N) were rendered anhydrous by coevaporating with pyridine, followed by toluene. The residue was dissolved in anhydrous THF (3 mL) and cooled in an ice-bath. Diisopropyl ethyl amine (0.2 mL, 3 eq.), BopCl (190 mg, 2 eq.), and 3-nitro-1,2,4-triazole (81 mg, 2 eq.) were added, and the mixture was stirred at 0° C. for 90 mins. The mixture was diluted with EtOAc, washed with sat. aq. $NaHCO_3$ and brine, and dried ($Na_2SO_4$). Purification on silica gel column with $CHCl_2$/i-PrOH (4-10% gradient) followed by RP-HPLC purification (A: 0.1% HCOOH in water, B: 0.1% HCOOH in MeCN) yielded compound 11 (28 mg, 12%). %-NMR (CDCl 3): δ 7.24 (d, 1H), 6.6 (br, 1H), 5.84 (d, 1H), 5.65-5.73 (m, 4H), 4.94 (m, 2H), 4.38 (m, 2H), 4.1 (b, 1H), 2.88 (d, 1H), 1.47 (d, 3H), 1.33 (m, 12H).

Example 2: Biological Activity

The antiviral activity of compounds was tested against the rat HEV replicon LA-B350/luc as described in Debing et al (Dis Model Mech 2016; 9:1203-10). To this end, Huh7 cells were electroporated with capped viral RNA produced from plasmid pLA-B350/luc, plated in 96-well plates and treated with each of compounds at selected concentrations. For virus control (VC), compound was omitted. After 3 days, luminescence produced by the secreted *Gaussia* luciferase was quantified using the Promega *Renilla* luciferase kit and corrected for background with a cell control (CC, viral RNA and compound omitted). The 50% effective concentration (EC50) is defined as the concentration of compound that causes a 50% reduction in the Luc signal compared to that of average corrected VC. The EC50 was based on two experiments and derived by a nonlinear regression fit in GraphPad using a two-parameter logistic model while keeping the slope variable.

For viability evaluation, medium was removed and cells were subsequently incubated with MTS/PMS solution (3-(4,5-dimethylthiazol-2-yl)-5-(3-carboxymethoxyphenyl)-2-(4-sulfophenyl)-2H-tetrazolium/phenazinemethosulfate), which is metabolized to produce a brown, water-soluble product that is quantified after 1 h at 37° C. by absorbance read-out at 498 nm. Obtained values are expressed as percent inhibition of untreated RNA-transfected control condition. The CC50 represents the concentration at which the metabolic activity of the cells would be reduced to 50% of the metabolic activity of untreated cells (and was based on two experiments and derived by a nonlinear regression fit in GraphPad using a two-parameter logistic model while keeping the slope variable).

The results demonstrate that compounds of Formula (I) are active against HEV (rat HEV replicon LA-B350/luc).

| Compound number | $EC_{50}$ (μM) | CI 95% (μM) |
|---|---|---|
| 1 | <0.00064 | NA |
| 2 | 0.0089 | 0.0017 to 0.031 |
| 3 | 0.0099 | 0.0025 to 0.029 |
| 4 | 0.036 | 0.021 to 0.061 |
| 5 | 0.046 | 0.018 to 0.11 |
| 6 | 0.023 | 0.0068 to 0.065 |
| 7 | 0.11 | 0.037 to 0.28 |
| 8 | 0.86 | 0.38 to 1.8 |
| 9 | 4.8 | 1.3 to 23 |
| 10 | 5.7 | 2.7 to 12 |
| 11 | 7.3 | 3.8 to 15 |

NA = not applicable

Reported values may be rounded to two significant figures

None of compounds 1-11 reached a CC50 at the highest tested concentration of 50 μM.

Example 3: HEV Genotype 3 Replicon Kernow-C1 p6/Luc

The antiviral activity of compounds was tested against the HEV Genotype 3 replicon Kernow-C1 p6/luc (Kernow-C1 p6: GenBank accession number JQ679013) as previously described (Debing Y, Emerson S U, Wang Y, Pan Q, Balzarini J, Dallmeier K, Neyts J. 2013. Ribavirin Inhibits In Vitro Hepatitis E Virus Replication through Depletion of Cellular GTP Pools and Is Moderately Synergistic with Alpha Interferon. Antimicrob Agents Chemother, 58:267-273). To this end, Huh7 cells were electroporated with capped in vitro transcribed Kernow-C1 p6/luc-RNA produced from MluI-digested plasmid DNA (Shukla P, Nguyen H T, Faulk K, Mather K, Torian U, Engle R E, Emerson SU. 2012. Adaptation of a genotype 3 hepatitis E virus to efficient growth in cell culture depends on an inserted human gene segment acquired by recombination. J. Virol. 86:5697-5707), seeded in 96-well plates containing serial dilutions of the test compounds. For virus control (VC) compound was omitted. After 4 days, luminescence produced by the secreted *Gaussia* luciferase was quantified using the Promega *Renilla* luciferase kit and corrected for background with a cell control (CC, viral RNA and compound omitted). The relative 50% effective concentration (EC50) is defined as the concentration of compound that causes a 50% reduction in the Luc signal, relative to the signal range. The relative EC50 was based on two experiments and derived by a nonlinear regression fit in GraphPad using a four-parameter logistic (4PL) model.

For viability evaluation, medium was removed and cells were subsequently incubated with MTS/PMS solution (3-

(4,5-dimethylthiazol-2-yl)-5-(3-carboxymethoxyphenyl)-2-(4-sulfophenyl)-2H-tetrazolium/phenazinemethosulfate), which is metabolized to produce a brown, water-soluble product that is quantified after 1 h at 37° C. by absorbance read-out at 498 nm. Obtained values are expressed as percentage of untreated RNA-transfected control condition. The relative CC50 represents the concentration at which the metabolic activity of the cells would be reduced to 50% of the metabolic activity of untreated cells and was based on two experiments and derived by a nonlinear regression fit in GraphPad using a four-parameter logistic (4PL) model.

The results demonstrate that compounds of Formula (I) are active against HEV Genotype 3 replicon Kernow-C1 p6/luc.

| Compound number | relative $EC_{50}$ (μM) | CI 95% (μM) |
|---|---|---|
| 1 | 0.013 | 0.0011 to 0.029 |
| 2 | 0.011 | 0.0082 to 0.014 |
| 3 | 0.012 | 0.011 to 0.014 |
| 4 | 0.0065 | 0.0025 to 0.011 |
| 5 | 0.022 | 0.015 to 0.031 |
| 6 | 0.026 | 0.014 to 0.048 |
| 7 | 0.042 | 0.023 to 0.069 |
| 8 | 0.220 | 0.085 to 0.52 |
| 9 | >50 | NA |
| 10 | 1.3 | 0.79 to 2.50 |
| 11 | 0.72 | 0.30 to 4.5 |

Reported values may be rounded to two significant figures.

All compounds except compound 1 did not reach a relative CC50 at the highest tested concentration of 50 μM. At higher concentrations, toxicity may be observed.

Compounds disclosed herein are potent and, without being bound by any theory, it is understood that this may translate in an in vivo setting to an effective therapy for the treatment of a hepatitis E infection.

Example 4: In Vivo Efficacy in a HEV Athymic Nude Rats (HEV Strain LA-B350)

Prior to the in vivo efficacy study, a new batch of the rat HEV virus is prepared from the livers of 10 infected athymic nude rats. This freshly prepared virus batch is used in all in vivo studies.

Thaw a vial containing 10% liver homogenate of the freshly prepared rat HEV. Dilute the virus stock ten times in PBS, corresponding to approximately 2×107 viral RNA copies. Infect the athymic nude rats with 200 μL of the diluted virus stock via intravenous injection in the tail vein. Start treating the rats 1 hour prior to infection and continue once daily with the treatment until day 14 pi. Weigh the rats and check for clinical signs every day until the end of the experiment (day 21 pi). From day 1-14 pi, collect blood once a week and faeces every 3 days to quantify the viral load by RT-qPCR. From day 15-21 pi, collect faeces every 3 days for quantification of the viral load. On day 21 pi, rats are euthanized via i.p injection of dolethal and blood collected via cardiac puncture and, upon intracardiac perfusion with PBS, the liver. Blood and liver are analysed for the presence of viral RNA (RT-qPCR) and histopathology.

| Group | Number of rats | Dose (mg/kg) | Frequency | MOA |
|---|---|---|---|---|
| Vehicle | 6 | — | QD | Oral gavage |
| Ribavirin | 6 | 30 mg/kg | QD | i.p. |
| Test compound | 6 | High dose (e.g. 200 mg/kg) | QD | Oral gavage |
| Test compound | | Medium dose (e.g. 70 mg/kg) | QD | Oral gavage |
| Test compound | 6 | Low dose (e.g. 20 mg/kg) | QD | Oral gavage |
| Sofosbuvir | 6 | To be determined | QD | Oral gavage |

| Day 0 | Day 1-14 pi | Day 15-20 pi | Day 21 pi |
|---|---|---|---|
| Weigh<br>Collect faeces & blood<br>Treat<br>Infect | Weigh<br>Check for clinical signs<br>Treat once daily<br>Collect faeces every 3 days<br>Collect blood once a week | Weigh<br>Check for clinical signs<br>Collect faeces every 3 days | Weigh<br>Check for clinical signs<br>Sacrifice<br>Collect blood, liver &<br>faeces for RT-qPCR &<br>histology |

Study Design:

Day-1 or -2 pi: Divide 5-week-old (110-130 g) homozygous female athymic nude Hsd:RH-Foxnlmnu rats (*Rattus norvegicus*, Envigo, Horst, The Netherlands) into 4-6 groups (5 animals/group); give them an ear tag.

Day 0 pi: Weigh the rats and treat via oral gavage or ip (ribavirin or IFN), according to the schedule above, starting 1 h before infection. Intravenous infection with 200 μL of 1% liver homogenate of rat HEV strain LA-B350 (corresponding to approximately 2×107 viral RNA copies).

Day 1-14 pi: Weigh rats daily and treat once daily. Animals are monitored for mobility, care and behavior. Faeces will be collected every 3 days and blood (serum) will be collected once a week from the tail for quantification of viral load by RT-qPCR. When reaching humane endpoints (hunched back, ruffled fur, ≥20% weight loss, lethargic), animals will be euthanized.

Day 15-20 pi: Weigh rats daily. Animals are monitored for mobility, care and behavior. Faeces will be collected every 3 days for quantification of viral load by RT-qPCR. When reaching humane endpoints (hunched back, ruffled fur, 20% weight loss, lethargic), animals will be euthanized.

Day 21 pi: Animals are euthanized: collect liver, blood (serum) and faeces.

Sample Processing:

Liver: 1) Quantification of viral load by RT-qPCR

2) Histological examination

Blood: Quantification of viral load by RT-qPCR

Faeces: Quantification of viral load by RT-qPCR

The application also comprises the following clauses, which may be claimed:

1. A compound for use in treating a hepatitis E infection in a subject in need thereof, wherein the compound is a compound of formula (I):

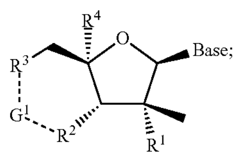

(I)

or a pharmaceutically acceptable salt thereof; wherein:

Base is selected from the group consisting of (b-1), (b-2), (b-3), (b-4), (b-5), (b-6), (b-7) and (b-8):

(b-1)

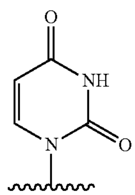

(b-2)

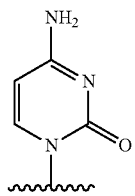

(b-3)

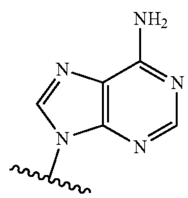

(b-4)

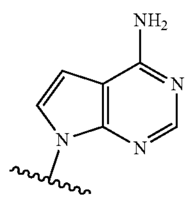

(b-5)

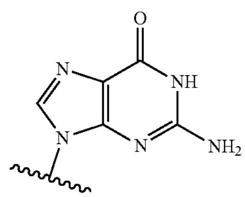

(b-6)

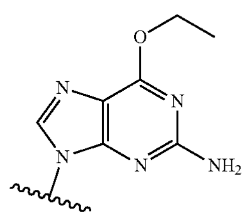

-continued (b-7)

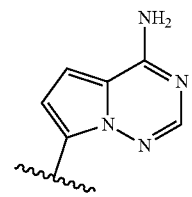

(b-8)

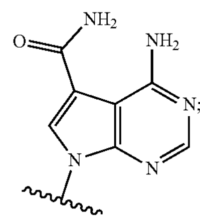

$R^1$ is selected from the group consisting of OH and F;

$G^1$ is absent, or $G^1$ is selected from the group consisting of (g-1), (g-2), and (g-3):

(g-1)

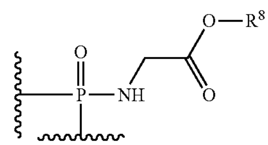

(g-2)

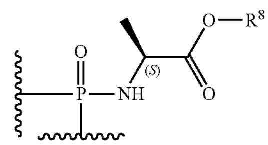

(g-3)

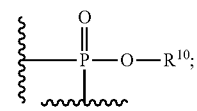

'--' is a bond in case $G^1$ is selected from the group consisting of (g-1), (g-2), and (g-3); and '--' is absent in case $G^1$ is absent;

$R^8$ is selected from the group consisting of C-4alkyl and $C_{3-6}$cycloalkyl;

$R^9$ is CI-4alkyl;

$R^{10}$ is selected from the group consisting of $C_{2-3}$alkenyl and $C_{3-6}$cycloalkyl; wherein when $G^1$ is absent;

$R^2$ is OH when $G^1$ is absent; and $R^2$ is —O— when $G^1$ is selected from the group consisting of (g-1), (g-2), and (g-3);

$R^3$ is —O— when $G^1$ is selected from the group consisting of (g-1), (g-2), and (g-3); and $R^3$ is selected from the group consisting of (f-1), (f-2) and (f-3) when $G^1$ is absent:

(f-1)

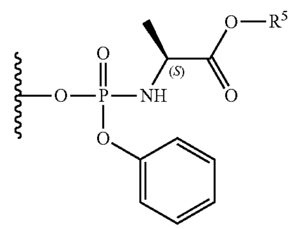

(f-2)

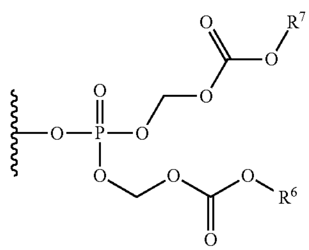

(f-3)

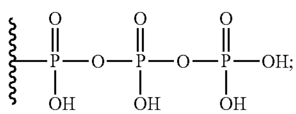

$R^5$ is selected from the group consisting of $C_{1-4}$alkyl and $C_{3-6}$cycloalkyl;

$R^6$ is selected from the group consisting of $C_{1-4}$alkyl and $C_{3-6}$cycloalkyl; and $R^7$ is $C_{1-4}$alkyl;

wherein when $G^1$ is present;

$R^2$ is O;

$R^3$ is O;

and $R^4$ is selected from the group consisting of H and F.

2. The compound for the use of clause 1, wherein Base is selected from the group consisting of (b-1) and (b-6).

3. The compound for the use of clause 1 or 2, wherein $G^1$ is absent and $R^3$ is selected from the group consisting of (f-1) and (f-2).

4. The compound for the use of clause 1 or 2, wherein $G^1$ is (g-1) and $R^8$ is CI-4alkyl.

5. The compound for the use of clause 1 or 2, wherein $G^1$ is (g-2).

6. The compound for the use of clause 1 or 2, wherein $G^1$ is (g-3) and $R^{10}$ is selected from $C_{1-4}$alkyl and $C_{2-3}$alkenyl.

7. The compound for the use of clause 1, wherein the compound is selected from the group consisting of:

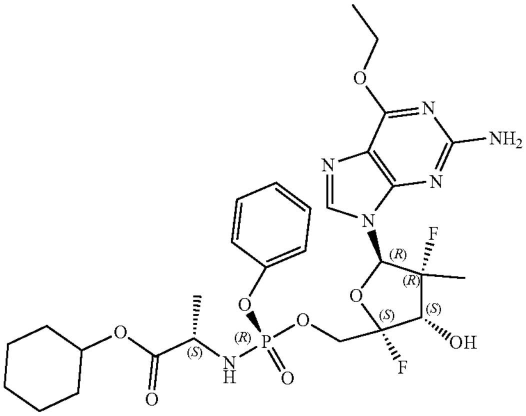

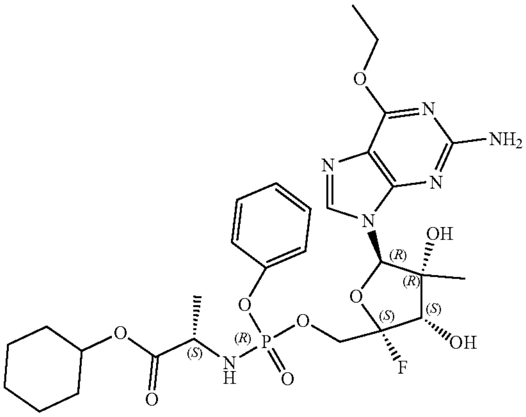

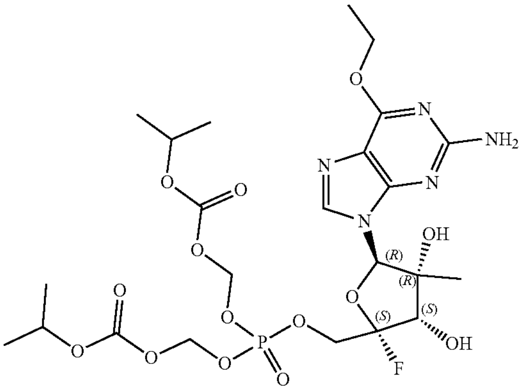

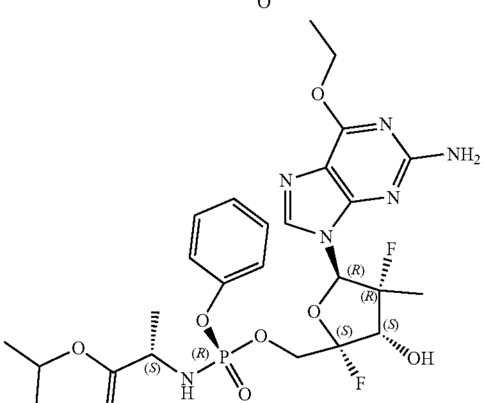

-continued

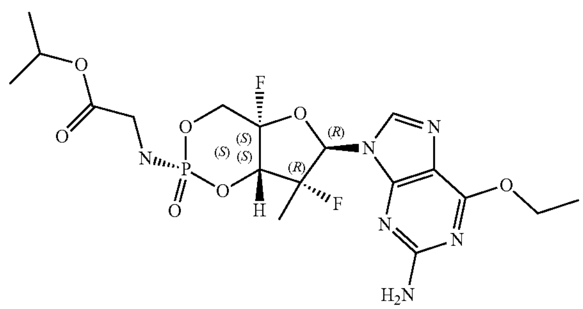

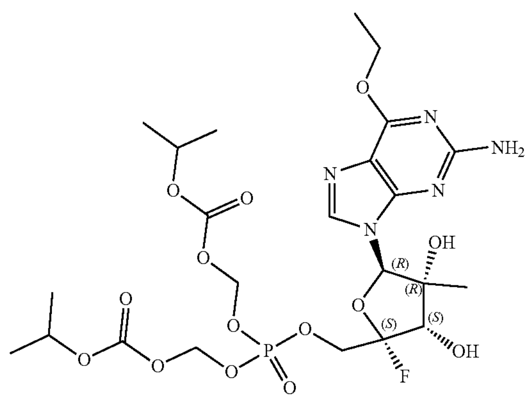

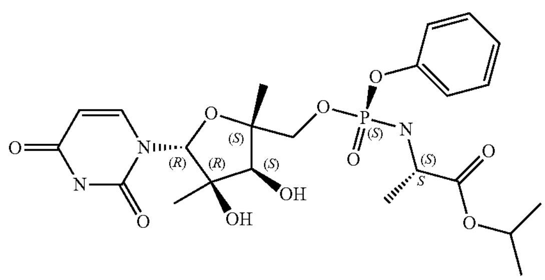

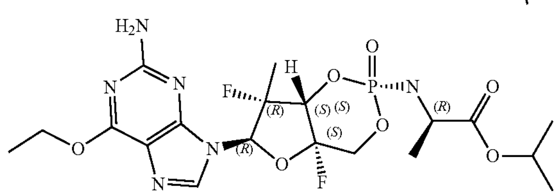

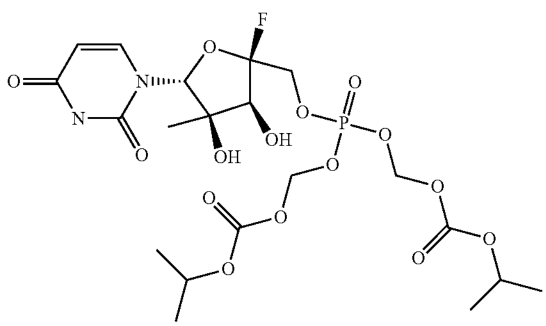

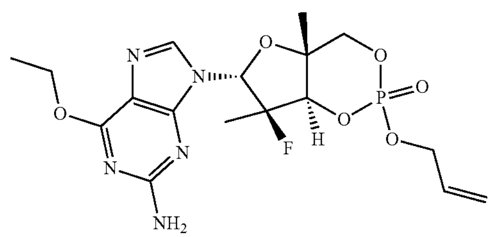

-continued

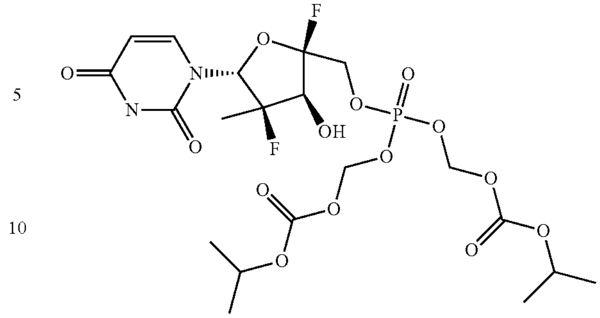

8. The compound for the use of clause 1, wherein the compound is:

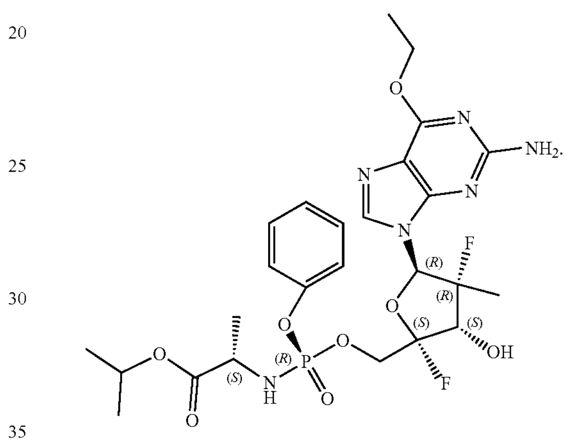

9. The compound for the use of any one of clauses 1-5, wherein the compound is not isopropyl (2S)-2-[[[(2R,3R,4R,5R)-5-(2,4-dioxopyrimidin-1-yl)-4-fluoro-3-hydroxy-4-methyltetrahydrofuran-2-yl]methoxy-phenoxy-phosphoryl]amino]propanoate:

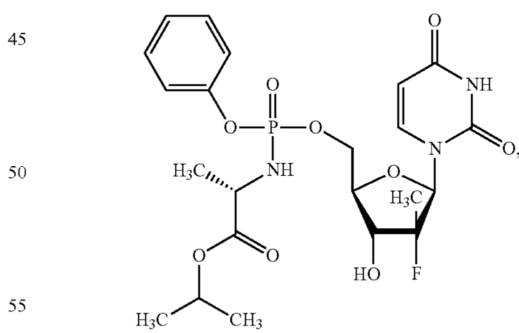

or a pharmaceutically acceptable salt thereof.

10. A pharmaceutical composition for use in treating a hepatitis E infection in a subject in need thereof, which comprises the compound as defined in any one of clauses 1-9, and a pharmaceutically acceptable vehicle.

11. The compound for the use of any one of clauses 1-9, or the pharmaceutical composition for the use of clause 10, wherein the hepatitis E infection is a chronic HEV infection.

12. The compound for the use of any one of clauses 1-9, or the pharmaceutical composition for the use of clause 10, wherein the HEV infection is of genotype 1, genotype 2 or genotype 3.

13. The compound for the use of any one of clauses 1-9, or the pharmaceutical composition for the use of clause 10, wherein the subject is a pregnant woman, an immune-compromised subject or immune-deficient subject.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A method for treating a hepatitis E virus (HEV) infection in a subject in need thereof, comprising administering a compound of formula (Ia) to the subject:

(Ia)

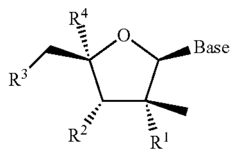

or a pharmaceutically acceptable salt thereof, wherein:

Base is (b-1) or (b-6):

(b-1)

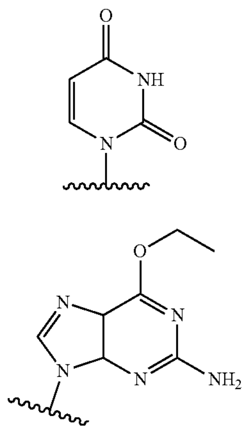

(b-6)

$R^1$ is OH or F;

$R^2$ is OH;

$R^3$ is (f-1), (f-2) or (f-3):

(f-1)

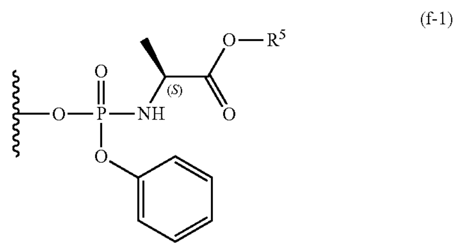

(f-2)

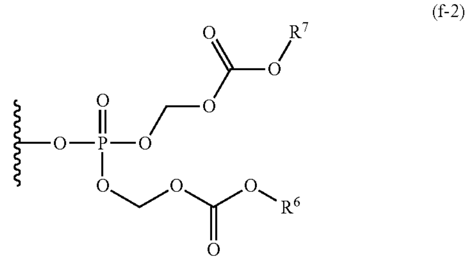

(f-3)

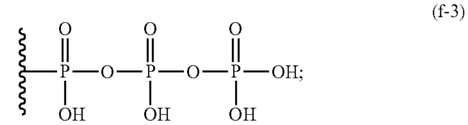

$R^4$ is F;

$R^5$ is $C_{1-4}$alkyl or $C_{3-6}$cycloalkyl;

$R^6$ is $C_{1-4}$alkyl or $C_{3-6}$cycloalkyl; and $R^7$ is $C_{1-4}$alkyl.

2. The method of claim 1, wherein the compound is:

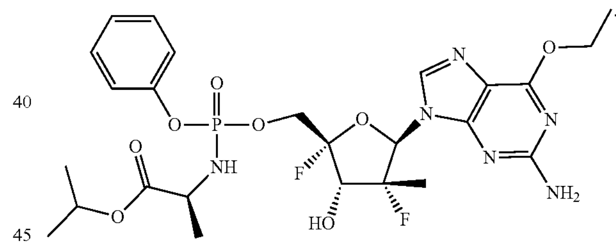

3. The method of claim 1, wherein the compound is:

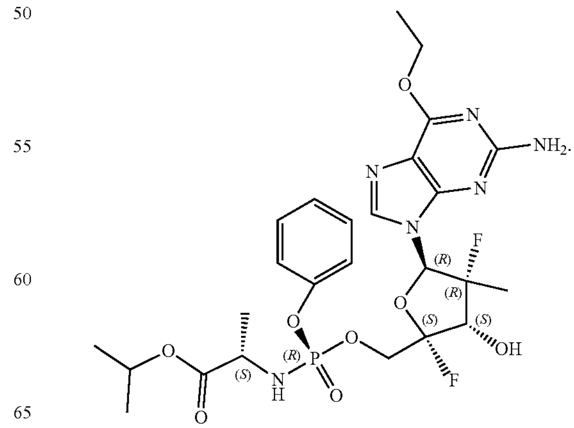

4. The method of claim 1, wherein the hepatitis E infection is a chronic HEV infection.

5. The method of claim 1, wherein the HEV infection is of genotype 1, genotype 2 or genotype 3.

6. The method of claim 1, wherein the subject is a pregnant woman, an immune-compromised subject or immune-deficient subject.

7. The method of claim 1, wherein the compound is administered to the subject in a pharmaceutical composition.

* * * * *